(12) United States Patent
Tajima

(10) Patent No.: US 9,521,987 B2
(45) Date of Patent: Dec. 20, 2016

(54) RADIATION IMAGING SYSTEM AND OPERATING METHOD THEREOF

(71) Applicant: FUJIFILM Corporation, Tokyo (JP)

(72) Inventor: Takashi Tajima, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 291 days.

(21) Appl. No.: 14/511,268

(22) Filed: Oct. 10, 2014

(65) Prior Publication Data

US 2015/0055753 A1 Feb. 26, 2015

Related U.S. Application Data

(63) Continuation of application No. PCT/JP2013/061049, filed on Apr. 12, 2013.

(30) Foreign Application Priority Data

Apr. 13, 2012 (JP) .................. 2012-091619

(51) Int. Cl.
H05G 1/42 (2006.01)
A61B 6/00 (2006.01)
A61B 6/08 (2006.01)

(52) U.S. Cl.
CPC .................. *A61B 6/542* (2013.01); *A61B 6/08* (2013.01); *A61B 6/4283* (2013.01); *A61B 6/547* (2013.01); *A61B 6/4452* (2013.01); *A61B 6/588* (2013.01)

(58) Field of Classification Search
CPC ......... A61B 6/542; A61B 6/08; A61B 6/4283; A61B 6/547; A61B 6/588; A61B 6/4452
USPC ............................ 378/62, 97, 108
See application file for complete search history.

(56) References Cited

U.S. PATENT DOCUMENTS

2005/0169425 A1* 8/2005 Takasawa ................ A61B 6/00
378/97

FOREIGN PATENT DOCUMENTS

| EP | 1388740 A2 | 2/2004 |
|---|---|---|
| JP | 6-217973 A | 8/1994 |
| JP | 2004-73256 A | 3/2004 |
| JP | 2005-211514 A | 8/2005 |
| JP | 2008-125610 A | 6/2008 |
| JP | 2011-15899 A | 1/2011 |
| JP | 2011-139761 A | 7/2011 |

OTHER PUBLICATIONS

International Search Report, issued in PCT/JP2013/061049, dated May 28, 2013.

(Continued)

*Primary Examiner* — Courtney Thomas
(74) *Attorney, Agent, or Firm* — Birch, Stewart, Kolasch & Birch, LLP

(57) ABSTRACT

A console acquires a displacement amount of an X-ray source from a displacement amount detector. In the case where an electronic cassette having an image detector is not appropriately positioned with respect to a body part to be imaged, a position of the X-ray source is changed in accordance with a position of the body part to be imaged. A dose measurement field position determining unit specifies a current relative position between the X-ray source and the electronic cassette having the image detector based on a displacement amount. The dose measurement field position determining unit determines a position of a dose measurement field based on the specified current relative position.

18 Claims, 19 Drawing Sheets

(56) References Cited

OTHER PUBLICATIONS

Written Opinion of the International Searching Authority, issued in PCT/JP2013/061049, dated May 28, 2013.
Japanese Office Action, dated Sep. 16, 2015, for Japanese Application No. 2014-510208, with an English translation.
International Preliminary Report on Patentability and English translation of the Written Opinion of the International Searching Authority (Forms PCT/IB/338, PCT/IB/373 and PCT/ISA/237), mailed Oct. 23, 2014, for International Application No. PCT/JP2013/061049.

* cited by examiner

FIG. 8

| BODY PART TO BE IMAGED | TUBE VOLTAGE (kV) | TUBE CURRENT (mA) | DOSE MEASUREMENT FIELD | IRRADIATION STOP THRESHOLD VALUE |
|---|---|---|---|---|
| ... | ... | ... | ... | ... |
| CHEST | V1 | I1 | ▫▫ | th1 |
| ABDOMEN | V2 | I2 | ▫ | th2 |
| ... | ... | ... | ... | ... |

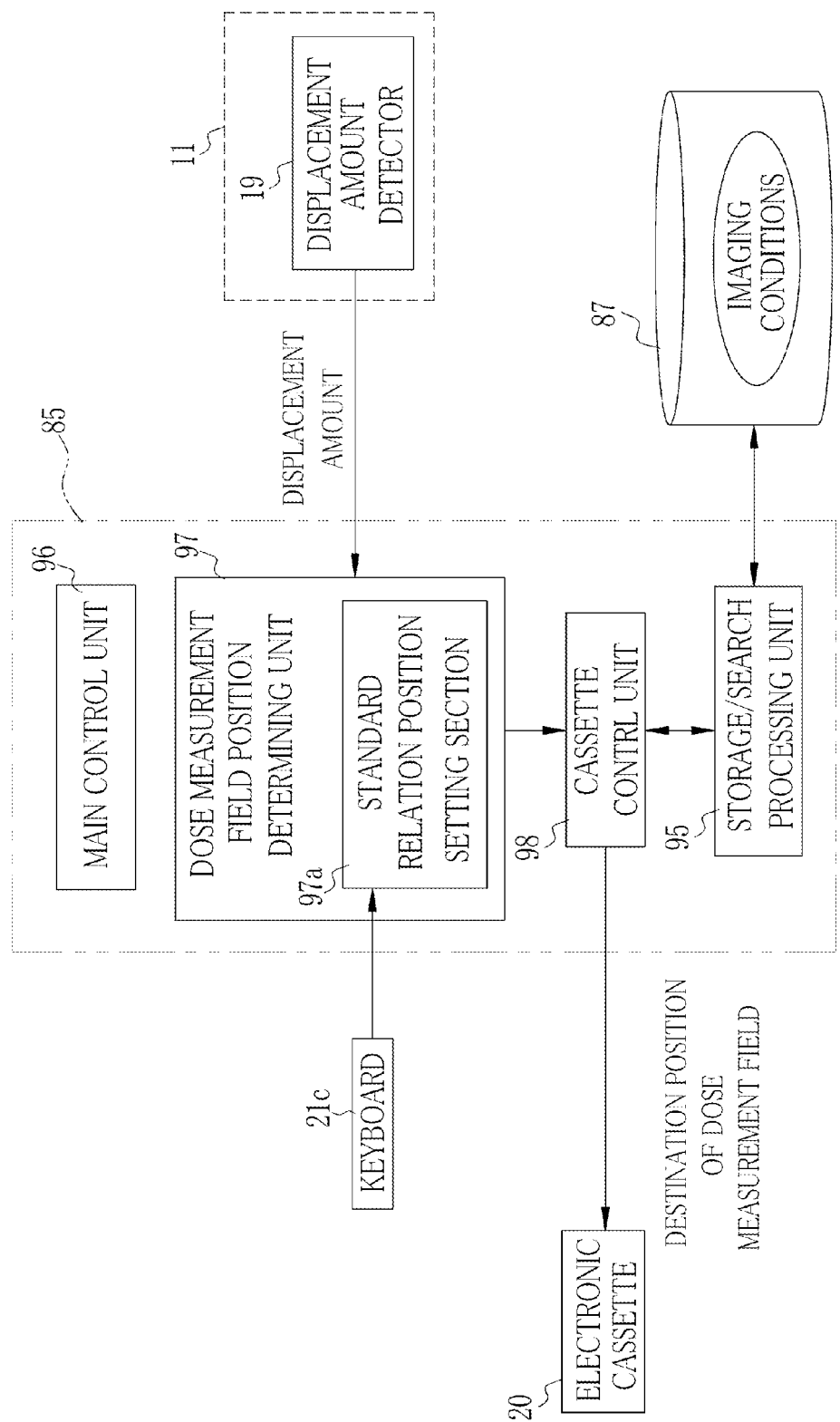

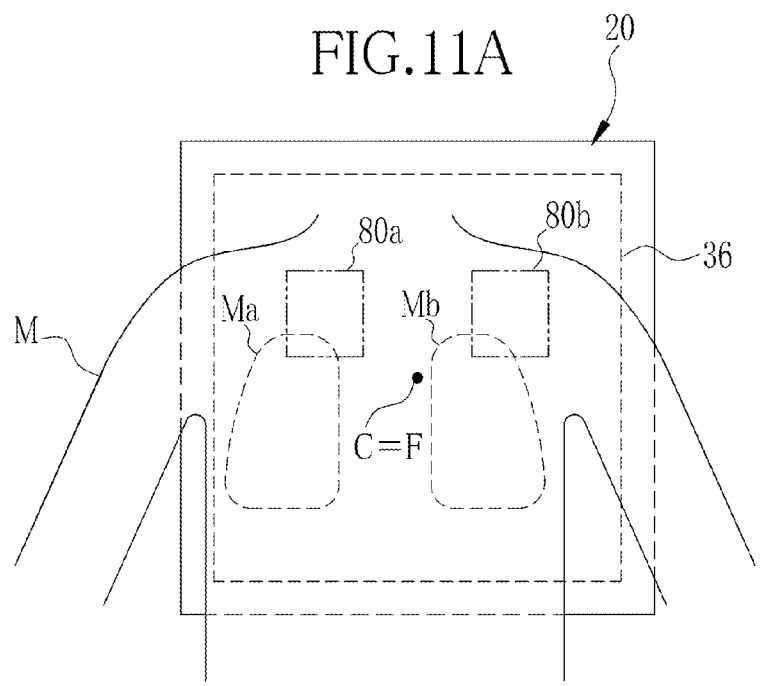
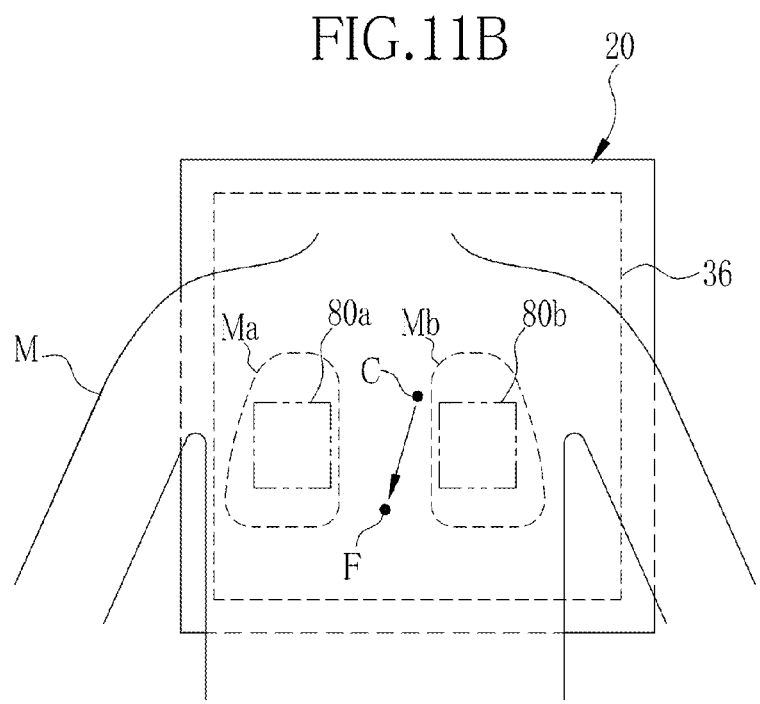

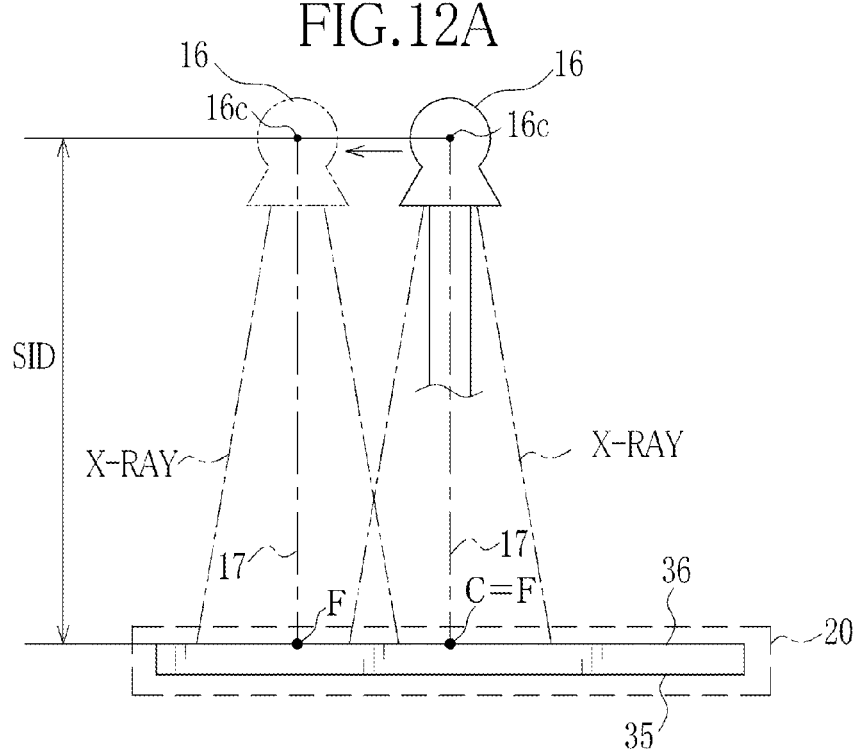
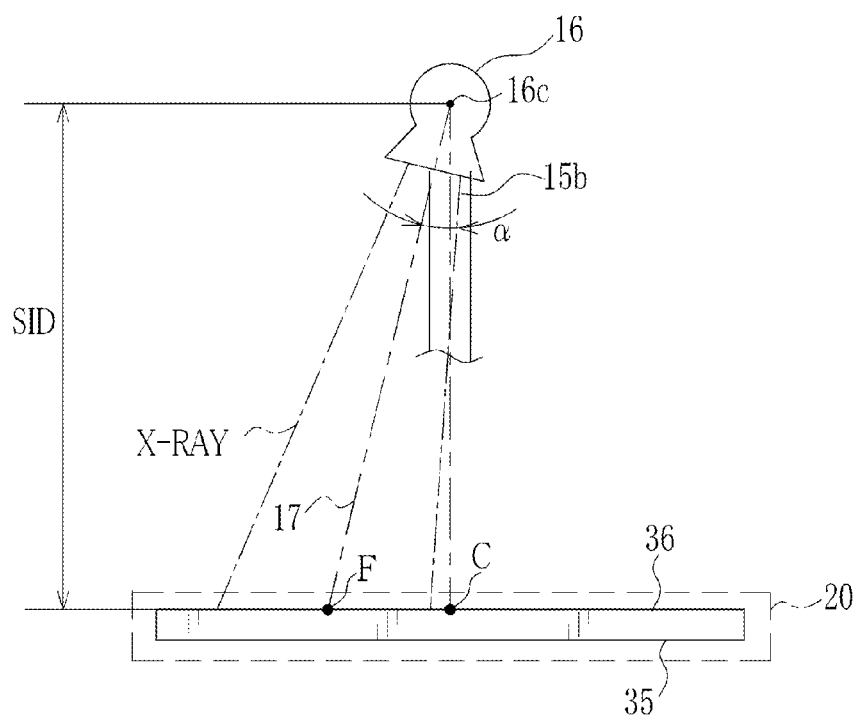

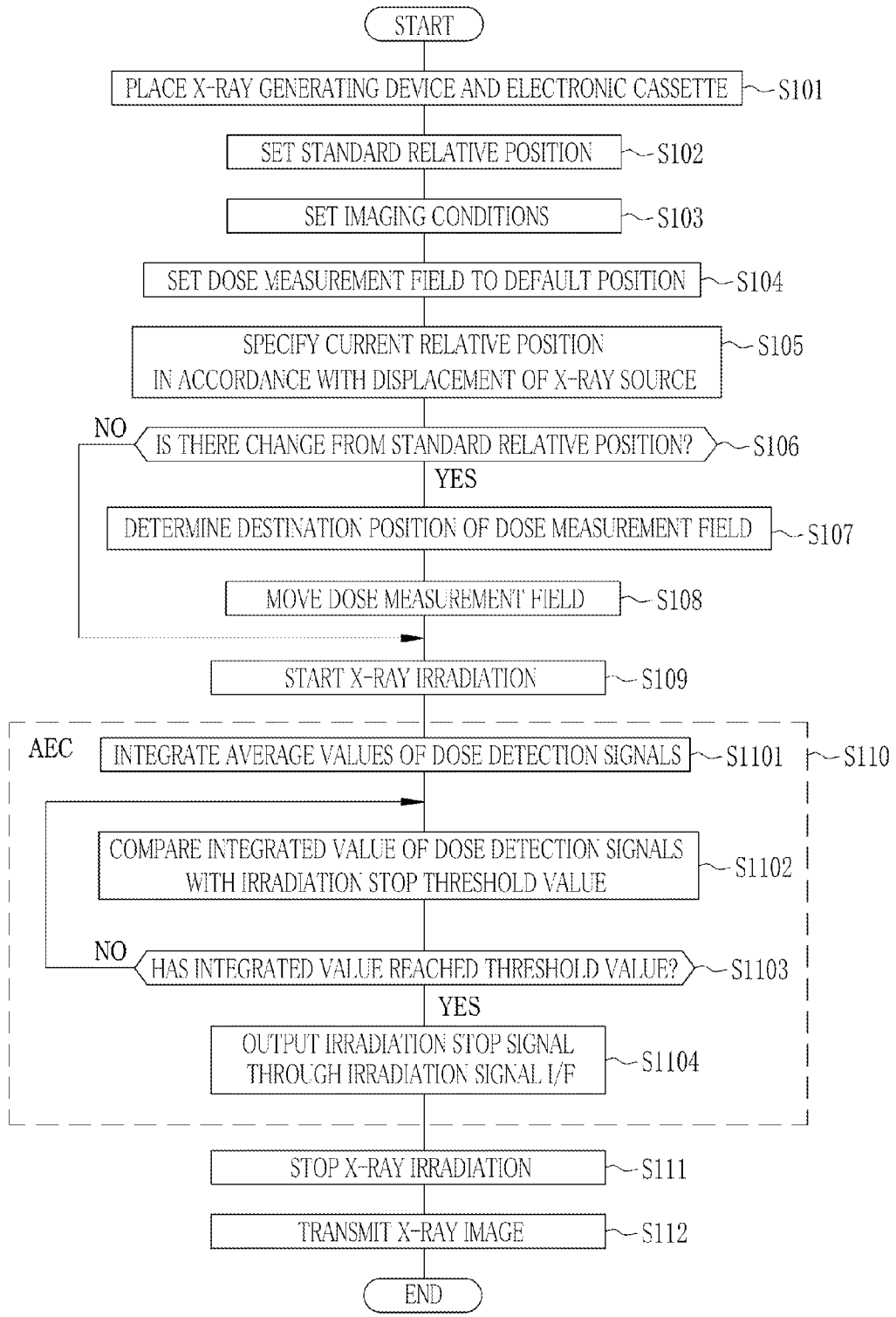

RADIATION IMAGING SYSTEM AND OPERATING METHOD THEREOF

CROSS-REFERENCE TO RELATED APPLICATIONS

This application is a Continuation of PCT International Application No. PCT/JP2013/061049 filed on Apr. 12, 2013, which claims priority under 35 U.S.C §119(a) to Japanese Patent Application No, 2012-091619 filed Apr. 13, 2012. The above application is hereby expressly incorporated by reference, in its entirety, into the present application.

BACKGROUND OF THE INVENTION

1. Field of the Invention

The present invention relates to a radiation imaging system having a function of performing exposure control of a radiation image, and an operating method thereof.

2. Description Related to the Prior Art

In a medical field, an X-ray imaging system using radiation such as X-rays is known. The X-ray imaging system is constituted of an X-ray generating device for generating X-rays and an X-ray imaging apparatus for acquiring an X-ray image of an object (i.e. patient) from the X-rays that have passed through the object.

The X-ray generating device includes an X-ray source for irradiating the X-rays to the object, a source controller for controlling the operation of the X-ray source, and an irradiation switch for inputting a command for actuating the X-ray source to the source controller. The X-ray source has an X-ray tube, in which thermal electrons emitted from a cathode are made to collide with an anode (target), such that the X-rays are irradiated from a focus located on the anode with which thermal electrons collide. The X-rays are radially irradiated as X-ray beams from the focus to the object. Further, the X-ray generating device includes a displacement mechanism which enables linear movement and rotation of the X-ray source, and is configured to arbitrarily change the X-ray irradiation point and the X-ray irradiation angle of the X-ray source.

The X-ray imaging apparatus includes an X-ray image detecting device for detecting the X-ray image upon receiving the X-rays having passed through the object, and a console for controlling the operation of the X-ray image detecting device and storing and displaying the X-ray image. An X-ray image detecting device using an image detector referred to as a FPD (flat panel detector) has been widely spread. The FPD has an imaging surface, on which pixels for accumulating electric charges corresponding to the received X-ray dose are arranged in a matrix, and detects the X-ray image as the electrical signal. The image detector accumulates signal charges on a pixel-by-pixel basis, and converts the accumulated electric charges into a voltage signal by a signal processing circuit. Thereby, the image detector detects the X-ray image of the object, and outputs the X-ray image as digital image data.

There are a stationary-type X-ray image detecting device and a portable-type X-ray image detecting device. In the stationary-type X-ray image detecting device, the image detector is incorporated into an imaging table. In the portable-type X-ray image detecting device, the image detector is incorporated into a potable flat housing. The stationary-type X-ray image detecting device is intended for imaging a patient in a standing posture, or intended for imaging a patient in a lying posture. In the case where the stationary-type X-ray image detecting device is intended for imaging a patient in a standing posture, the image detector is movable in a vertical direction. In the case where the stationary-type X-ray image detecting device is intended for a patient in a lying posture, the image detector is movable in a horizontal direction. In accordance with a body frame of the patient and a body portion to be imaged, the position of the image detector is adjusted.

The portable-type X-ray image detecting device is referred to as an electronic cassette. The electronic cassette is detachably attached to an existing imaging stand designed for a film cassette and an imaging plate (IP) cassette, or a dedicated imaging table, and used. Otherwise, the electronic cassette may be used independently without using the imaging table. For example, the electronic cassette may be brought into a hospital room of a patient who cannot move to an X-ray examination room, and put on a bed on which the patient is lying, so as to be used. In order to perform X-ray imaging in the hospital room, a medical equipment carrier as the X-ray generating device mounted on a wagon so as to be movable, and the electronic cassette are brought into the hospital room. The electronic cassette is inserted between the patient's body and the bed, and the medical equipment carrier is placed beside the bed.

Irrespective of whether the X-ray image detecting device is the stationary-type or the portable-type, positioning operation for determining a relative positional relationship among the X-ray source, the X-ray image detecting device, and the body part of the patient to be imaged is performed as preparation for the X-ray imaging, prior to the X-ray imaging. For example, at first, the relative position between the patient and the X-ray image detecting device is adjusted such that the center of the body part of the patient to be imaged and center of the imaging surface of the image detector are coincident with each other. Next, the relative position between the X-ray source and the X-ray image detecting device is adjusted such that the center of the imaging surface of the image detector and the center of the X-ray beam (hereinafter referred to as main ray) irradiating from the X-ray source are coincident with each other. The main ray corresponds to the center of the irradiation range of the X-ray source. Accordingly, the relative positional relationship among the X-ray source, the imaging surface of the image detector, and the body part of the patient to be imaged is determined appropriately.

Further, some X-ray imaging systems perform an automatic exposure control (hereinafter, referred to as AEC), in which the dose of X-rays having passed through the patient is detected by a dose detection sensor, and when an integrated value of the dose of X-rays achieves a predetermined threshold level, irradiation of the X-ray by the X-ray generating device is stopped, in order to perform exposure control of the X-ray image (see, for example, Japanese Patent Application Laid-open No. 2011-139761 and U.S. Pat. No. 5,539,798 (corresponding to Japanese Patent Application Laid-open No. 6(1994)-217973). Japanese Patent Application Laid-open No. 2011-139761 discloses an X-ray imaging system including an X-ray image detecting device using an image detector, and the X-ray imaging system performs the AEC using some of pixels in an imaging surface of the image detector as dose detection sensors. In the AEC, at least one of the dose detection sensors is selected, and thereby a dose measurement field is set as a field in which the dose of X-ray is measured. In the AEC, since it is necessary to measure the dose of the X-ray having passed through the patient, it is required to set the dose measurement field to be opposed to the body part of the patient to be imaged in the imaging surface of the image detector.

The X-ray imaging system disclosed in Japanese Patent Application Laid-open No. 2011-139761 includes an optical camera provided to the X-ray source, an image processor for extracting a contour of the body part of the patient to be imaged from an optical image of the patient captured by the optical camera, and a dose measurement field setting circuit for setting a dose measurement field within the extracted contour of the body part to be imaged. According to the X-ray imaging system disclosed in Japanese Patent Application Laid-open No. 2011-139761, positioning operation is performed appropriately such that the main ray of the X-ray source, the center of the imaging surface of the image detector, and the center of the body part of the patient to be imaged are coincident with each other, and in such a state, an optical image of the patient is captured by the optical camera, so as to set the dose measurement field within the contour of the body part to be imaged. The body part to be imaged includes many parts such as cephalic region, breast region, and extremities, and therefore the contour varies depending on the body part to be imaged. In the case where the contour of the body part to be imaged is extracted by using the optical camera in the same manner as the X-ray imaging system disclosed in Japanese Patent Application Laid-open No. 2011-139761, it is possible to contain the dose measurement field within the contour of the body part to be imaged even if the contour of the body part to be imaged varies.

U.S. Pat. No. 5,539,798 discloses an X-ray imaging system with use of an X-ray film. According to U.S. Pat. No. 5,539,798, it is also disclosed that an optical image of a patient is captured by using an optical camera provided to an X-ray source, a contour of a body part to be imaged is extracted from the captured optical image through an image processing, and a dose measurement field for AEC is set within the contour of the body part to be imaged in accordance with the extracted contour, as in the case of Japanese Patent Application Laid-open No. 2011-139761.

However, the X-ray imaging system disclosed in each of Japanese Patent Application Laid-open No. 2011-139761 and U.S. Pat. No. 5,539,798 relates to a technique based on the presumption that the X-ray source, the image detector, and the patient are appropriately positioned. In the case where the center of the imaging surface of the image detector and the center of the body part of the patient to be imaged are not coincident with each other, and the image detector and the body part of the patient to be imaged are not appropriately positioned, for example, there is a problem in that the imaging system in each of Japanese Patent Application Laid-open No. 2011-139761 and U.S. Pat. No. 5,539, 798 cannot be adopted.

In the case where the image detector and the body part of the patient to be imaged are appropriately positioned, the center of the X-ray source, the center of the image detector, and the center of the body part of the patient to be imaged are coincident with each other. Therefore, the center of the optical image captured by using the optical camera provided to the X-ray source corresponds to the center of the imaging surface of the image detector, and it becomes possible to appropriately set the position of the dose measurement field in the imaging surface of the image detector in accordance with the position of the body part to be imaged in the optical image.

In contrast, in the case where the center of the imaging surface of the image detector and the center of the body part of the patient to be imaged are not coincident with each other, the position of the X-ray source is moved in accordance with the position of the body part of the patient to be imaged such that the X-rays are irradiated to the body part of the patient to be imaged, and therefore the main ray of the X-ray source and the center of the imaging surface of the image detector are not coincident with each other. In this case, the center of the optical image captured by using the optical camera provided to the X-ray source corresponds to the center of the body part of the patient to be imaged, but does not correspond to the center of the imaging surface of the image detector. Accordingly, even if the position of the body part of the patient to be imaged is specified in the optical image, since the position of the body part to be imaged in the optical image does not correspond to the position of the imaging surface of the image detector, it is not possible to set the dose measurement field in the imaging surface appropriately.

Such a problem also occurs in the stationary-type X-ray image detecting device, but the frequency of occurrence of such a problem becomes prominent in the portable electronic cassette. In the case where the electronic cassette is used on the bed as described above, the electronic cassette is inserted between the patient and the bed. However, in some cases, it is not possible to change the posture of the patient to a large extent depending on the condition of the patient. In this case, it is not possible to perform positioning between the patient and the electronic cassette appropriately, and therefore the center of the body part of the patient to be imaged and the center of the imaging surface of the image detector are not coincident with each other.

According to Japanese Patent Application Laid-open No. 2011-139761 and U.S. Pat. No. 5,539,798, the method of setting the dose measurement field in the case where the body part of the patient to be imaged and the image detector are not appropriately positioned is not clearly disclosed nor suggested. Of course, it is possible to set the position of the dose measurement field appropriately in accordance with the position of the body part of the patient to be imaged, by applying the technique of setting the dose measurement field in part of the imaging surface as disclosed in Japanese Patent Application Laid-open No. 2011-139761, such that the dose measurement field can be set to an arbitrary position in the imaging surface by a manual operation. However, there is a problem in that such a manual operation is cumbersome.

SUMMARY OF THE INVENTION

In view of the foregoing, an object of the present invention is to provide a radiation imaging system capable of setting a dose measurement field at a position corresponding to a body part to be imaged by a simple operation even in a case where it is difficult to perform appropriate positioning between the body part of an object to be imaged and an image detector, and an operating method of the radiation imaging system.

To achieve the above and other objects of the present invention, a radiation imaging system of the present invention consists of a radiation generating device and a radiation image detecting device, and further includes a displacement mechanism and a displacement amount detector. The radiation generating device has a radiation source for irradiating radiation to an object. The radiation image detecting device has an image detector, a plurality of dose detection sensors, and a dose measurement field setting section. The image detector is formed with an imaging surface on which pixels for accumulating electric charges upon receiving the radiation are two-dimensionally arranged, and detects a radiation image of the object. The plurality of dose detection sensors are disposed on the imaging surface, and detect a dose of the radiation, so as to perform exposure control of the radiation image. The dose measurement field setting section sets a dose measurement field for the exposure control in the imaging surface by selecting at least one of the plurality of dose detection sensors. The displacement mechanism displaces a relative position between the radiation source and the image detector. The displacement amount detector detects a displacement amount of the relative position. The dose measurement field position determining section specifies a current relative position as a current position of the relative position based on the displacement amount, and determines a position of the dose measurement field set by the dose measurement field setting section based on the current relative position.

It is preferable that the radiation imaging system further includes a default position memory section for storing a default position of the dose measurement field, and a standard relative position setting section for setting a standard relative position as a standard of the relative position in association with the default position of the dose measurement field. The dose measurement field position determining section preferably determines a destination position to which the dose measurement field moves from the default position in accordance with the specified current relative position.

The main ray incident position is a position in the imaging surface of the image detector, on which a main ray as a center of a radiation beam irradiated from the radiation source is incident, and the dose measurement field position determining section calculates a movement distance of the main ray incident position from the standard relative position to the current relative position, and determines the destination position of the dose measurement field based on the calculated movement distance.

The standard relative position setting section preliminarily stores the standard relative position, which is a position at which a main ray as a center of a radiation beam irradiated from the radiation source is orthogonal to the imaging surface of the image detector as well as a main ray incident position for receiving entrance of the main ray in the imaging surface is coincident with a center of the imaging surface. The standard relative position setting section is preferably configured to set an arbitrary standard relative position.

The default position memory section preferably stores a default position of the dose measurement field for each body part of the object to be imaged.

It is preferable that the radiation imaging system further includes a notification section. The dose measurement field position determining section determines whether or not it is possible to move the dose measurement field from the default position to the destination position based on a size of the imaging surface, and the notification section preferably makes a notification in the case where the dose measurement field position determining section determines it impossible to move the dose measurement field. In this case, preferably, the default position memory section stores the default position of the dose measurement field for each body part of the object to be imaged, and the dose measurement field position determining section determines whether or not it is possible to move the dose measurement field for each body part of the object to be imaged.

The dose measurement field setting section is preferably configured to adjust a position of the dose measurement field irrespective of the displacement amount upon receiving a command for adjusting the position of the dose measurement field by a manual operation.

For example, the displacement mechanism includes a first displacement mechanism section for displacing the radiation source, the displacement amount detector detects a first displacement amount as a displacement amount of the radiation source displaced by the first displacement mechanism section, and the dose measurement field position determining section determines the destination position of the dose measurement field based on the first displacement amount. The first displacement amount includes at least one of a linear movement distance of the radiation source and a rotation angle of the radiation source.

Further, it is also possible that the displacement mechanism includes a first displacement mechanism section for displacing the radiation source and a second displacement mechanism section for displacing the image detector, and the displacement amount detector detects a first displacement amount of the radiation source displaced by the first displacement mechanism section and a second displacement amount of the image detector displaced by the second displacement mechanism section, such that the dose measurement field position determining section determines the destination position of the dose measurement field based on the first displacement amount and the second displacement amount.

The radiation imaging system further includes a displacement limit judging section for judging whether or not the image detector has reached a displacement limit thereof based on the second displacement amount. It is also possible that the dose measurement field position determining section does not determine the destination position of the dose measurement field in conjunction with the displacement of the relative position while the image detector does not reach the displacement limit thereof, and the dose measurement field position determining section determines the destination position of the dose measurement field in conjunction with the displacement of the relative position in the case where the image detector has reached the displacement limit thereof.

Preferably, switching is performed between a state in which the displacement of the relative position and the movement of the dose measurement field are in conjunction with each other and a state in which the displacement of the relative position and the movement of the dose measurement field are not in conjunction with each other.

The dose detection sensor is configured to use part of the pixels in the imaging surface, for example.

The radiation imaging system further includes a console for controlling the radiation image detecting device. The dose measurement field position determining section is provided in the console, and the dose measurement field setting section is provided in the radiation image detecting device, for example.

The radiation image detecting device is preferably an electronic cassette having the image detector contained in a portable housing.

An operating method of a radiation imaging system of the present invention is an operating method of a radiation imaging system including a radiation generating device and a radiation image detecting device. The radiation generating device has a radiation source for irradiating radiation to an object. The radiation image detecting device has an image detector, a plurality of dose detection sensors, and a dose measurement field setting section. The image detector is formed with an imaging surface on which pixels for accumulating electric charges upon receiving the radiation are arranged so as to detect a radiation image of the object. The plurality of dose detection sensors are disposed on the imaging surface to detect a dose of the radiation to perform exposure control of the radiation image. The dose measurement field setting section sets a dose measurement field for the exposure control in the imaging surface by selecting at least one of the plurality of dose detection sensors. The operating method of the radiation imaging system of the present invention includes a displacement amount detecting step and a dose measurement field position determining step. In the displacement amount detecting step, a displace amount of a relative position between the radiation source and the image detector is detected. In the dose measurement field position determining step, a current relative position as a current position of the relative position is specified based on the displacement amount, so as to determine a position of the dose measurement field set by the dose measurement field setting section based on the current relative position.

According to the present invention, the displacement amount of the relative position between the radiation source and the image detector is detected so as to specify the current relative position, and the position of the dose measurement field is determined in accordance with the specified current relative position. Therefore, it is possible to provide the radiation imaging system capable of setting the dose measurement field to the position corresponding to the body part to be imaged by the simple operation even in the case where the appropriate positioning of the image detector with respect to the body part of the object to be imaged is difficult, and the operating method of the radiation imaging system.

BRIEF DESCRIPTION OF DRAWINGS

For more complete understanding of the present invention, and the advantage thereof, reference is now made to the subsequent descriptions taken in conjunction with the accompanying drawings, in which:

FIG. 8 is a table showing imaging conditions set in the console;

FIG. 10 is an explanatory view showing a dose measurement field position determining unit;

FIG. 11A is an explanatory view showing a state in which the electronic cassette and a body part to be imaged are not appropriately positioned, and FIG. 11B is an explanatory view showing a state in which the position of the dose measurement field is moved from a default position;

FIG. 12A is an explanatory view showing a change in a main ray incident position in the case where the X-ray source is linearly moved, and FIG. 12B is an explanatory view showing a change in the main ray incident position in the case where the X-ray source is rotated;

FIG. 13 is a flowchart of an X-ray imaging procedure;

DESCRIPTION OF THE PREFERRED EMBODIMENTS

First Embodiment

Figure 1:
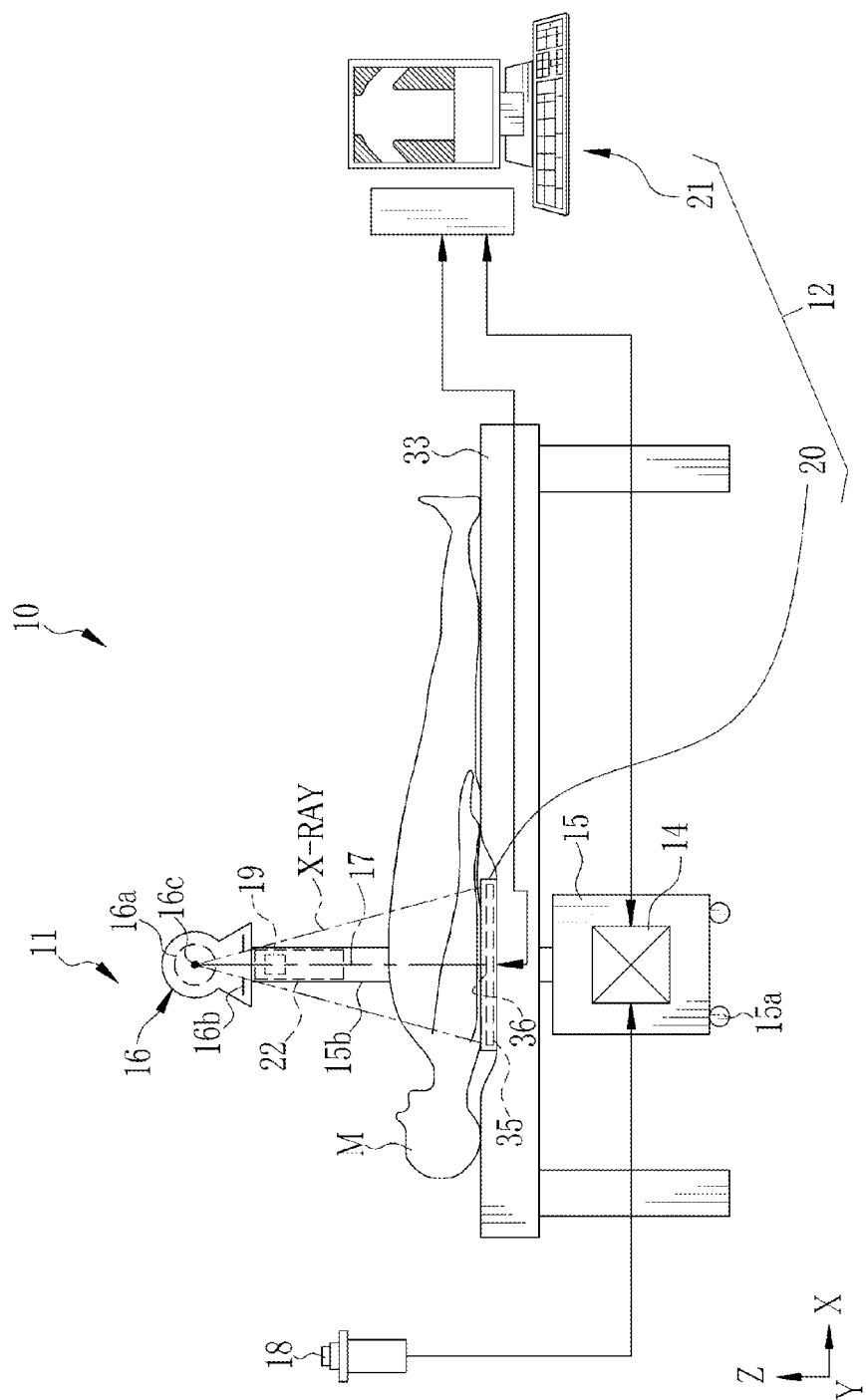
FIG. 1 is a schematic view showing the structure of an X-ray imaging system.

In FIG. 1, an X-ray imaging system 10 of the present invention consists of an X-ray generating device 11 for generating X-rays and an X-ray imaging apparatus 12 for acquiring an X-ray image from the X-rays having passed through a patient M as an object. The X-ray imaging apparatus 12 consists of an electronic cassette 20 as a portable X-ray image detecting device for detecting the X-ray image and a console 21 for controlling the electronic cassette 20.

The electronic cassette 20 consists of an image detector 35 which is a flat panel detector (FPD) and a portable flat housing containing the image detector 35. The planar shape of the housing is an approximately rectangle. In the case where X-ray imaging is performed on a patient who cannot move to an X-ray examination room, the electronic cassette 20 is inserted under a body of the patient M lying on a bed 33 in a hospital room, as shown in FIG. 1.

It is to be noted that a plane of the electronic cassette 20 has the same size as that of a film cassette and an IP cassette (also called as CR cassette), for example. The size of the plane of the electronic cassette 20 is compatible with International Standard ISO 4090:2001. Therefore, the electronic cassette 20 having such a size is attachable to an existing imaging stand designed for the film cassette and the IP cassette, to perform X-ray imaging.

A source controller 14, the electronic cassette 20, and the console 21 are connected to each other through a wired or wireless communicator so as to interact with each other.

The X-ray generating device 11 is movable so as to be used mainly in a place other than the X-ray examination room, such as a hospital room, and also referred to as a medical equipment carrier. The X-ray generating device 11 consists of a wagon 15 provided with tires 15a so as to be movable, an X-ray source 16 supported by a distal end of a pole 15b provided to the wagon 15 and used for irradiation of the X-rays, the source controller 14 incorporated into the wagon 15 so as to control the X-ray source 16, and an irradiation switch 18 for giving a command to start X-ray irradiation by the X-ray source 16.

The X-ray source 16 has an X-ray tube 16a for irradiating the X-rays and an irradiation field limiter (collimator) 16b for limiting an irradiation field of the X-rays irradiating from the X-ray tube 16a. The X-ray tube 16a has a cathode composed of a filament for emitting thermal electrons, and an anode (target) for irradiating the X-rays upon collision with the thermal electrons emitted from the cathode. The X-rays are radially irradiated as X-ray beams from a focus 16c located on the anode, with which thermal electrons collide, to the patient M. The reference numeral 17 denotes a main ray corresponding to the center of the X-ray beam. The irradiation field limiter 16b is composed of, for example, four lead plates for shielding the X-rays disposed in each side of a rectangle, such that a rectangular irradiation opening through which the X-rays pass is formed in the middle thereof. Shifting of the positions of the lead plates varies the size of the irradiation opening to limit the irradiation field.

The pole 15b is provided with a displacement mechanism 22 for displacing the X-ray source 16 relative to the pole 15b. The displacement mechanism 22 includes a movement mechanism for moving the X-ray source 16 in a horizontal direction (X and Y directions), a mechanism for changing the height of the X-ray source 16 (the position of the X-ray source 16 in a Z direction) by telescopically adjusting the length of the pole 15b, and a rotation mechanism for rotating the X-ray source 16 relative to the pole 15b so as to change the irradiation angle.

Figure 2A:
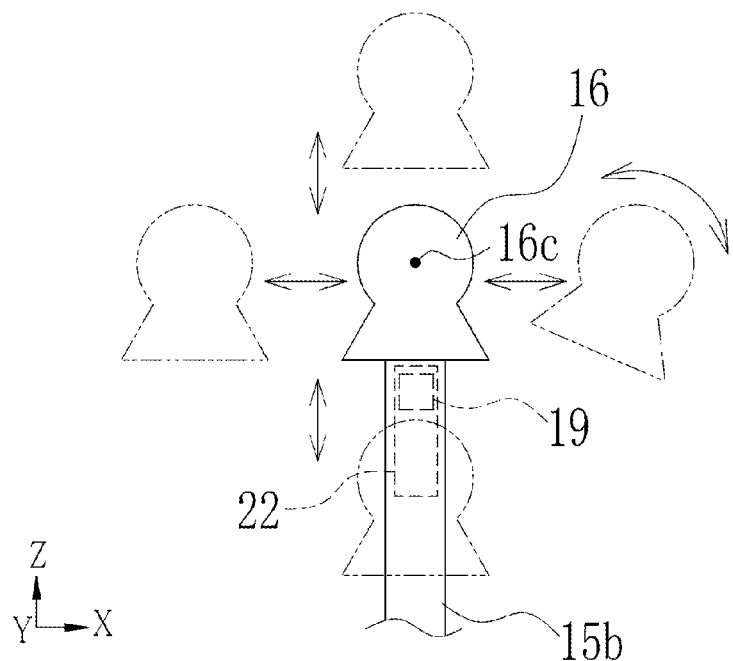
FIG. 2A is an explanatory view showing a displacement direction of an X-ray source.

Specifically, as shown by chain double-dashed lines in FIG. 2A, the X-ray source 16 is movable by the displacement mechanism 22 in the Z direction as a vertical direction, in the X direction orthogonal to the Z direction, and in the Y direction orthogonal to the Z direction and X direction. Further, the X-ray source 16 is rotatable around a Y axis by the displacement mechanism 22, and capable of rotating relative to the pole 15b. Thereby, it is possible to change the X-ray irradiation angle such that the X-rays are irradiated to the patient M in an oblique direction. For example, the wagon 15 is placed beside the bed 33 in the hospital room, and the position of X-ray source 16 is adjusted to be located above the patient M lying on the bed 33. The displacement mechanism 22 includes a displacement amount detector 19 for detecting a linear movement distance of the X-ray source 16 in the X, Y, and Z directions and a rotation angle of the X-ray source 16 around the Y axis as a displacement amount of the X-ray source 16.

Figure 2B:
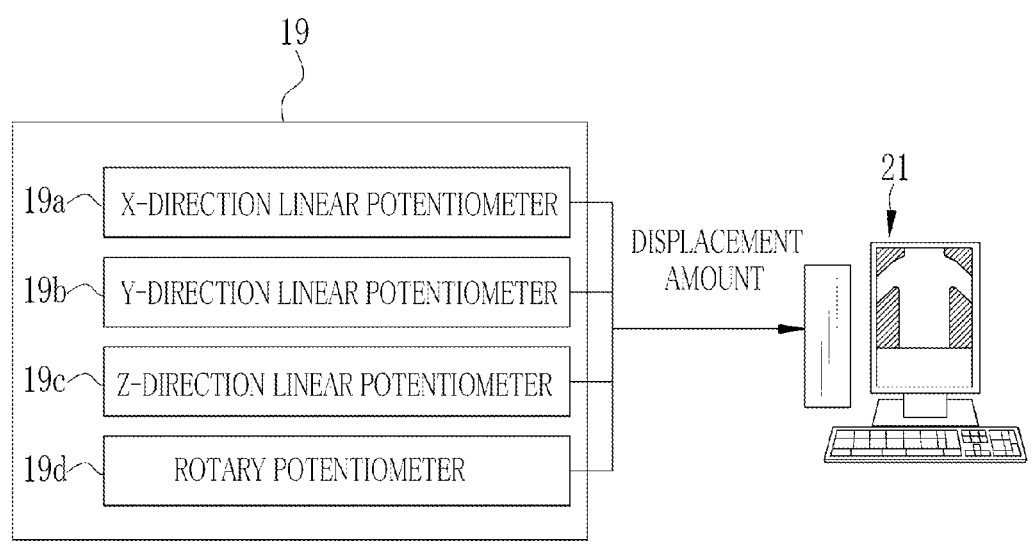
FIG. 2B is an explanatory view showing a displacement amount detector.

As shown in FIG. 2B, the displacement amount detector 19 is composed of a linear potentiometer 19a for detecting the linear movement distance in the X direction, a linear potentiometer 19b for detecting the linear movement distance in the Y direction, a linear potentiometer 19c for detecting the linear movement distance in the Z direction, and a rotary potentiometer 19d for detecting the rotation angle of the X-ray source 16 around the Y axis. Each of the potentiometers is, as well known, composed of a variable resistor and a voltage output circuit for outputting voltage corresponding to a resistance value of the variable resistor. Upon the displacement of X-ray source 16, each of the potentiometers 19a to 19d outputs an output value corresponding to the displacement of the X-ray source 16 as a displacement amount of the X-ray source 16 to the console 21.

The output value from each of the potentiometers 19a to 19d is information containing not only the movement distance and rotation amount but also the movement direction and the rotation direction of the X-ray source 16. For example, the output value from the X-direction linear potentiometer 19a is increased in the case where the movement direction is rightward, and decreased in the case where the movement direction is leftward, with respect to a standard value. It is possible to detect the movement direction and the rotation direction by checking whether the output value is increased or decreased with respect to the standard value. The console 21 specifies a current relative position between the X-ray source 16 and the electronic cassette 20 based on the displacement amount outputted from the displacement amount detector 19.

Here, the relative position between the X-ray source 16 and the electronic cassette 20 means the positional relationship between the irradiation position and the irradiation angle of the X-ray source 16 and an X-ray incident surface in the housing of the electronic cassette 20. Further, as the X-ray incident surface of the electronic cassette 20 is in parallel with an imaging surface 36 of the image detector 35, the relative position between the X-ray source 16 and the electronic cassette 20 corresponds to the relative position between the X-ray source 16 and the image detector 35.

Figure 3:
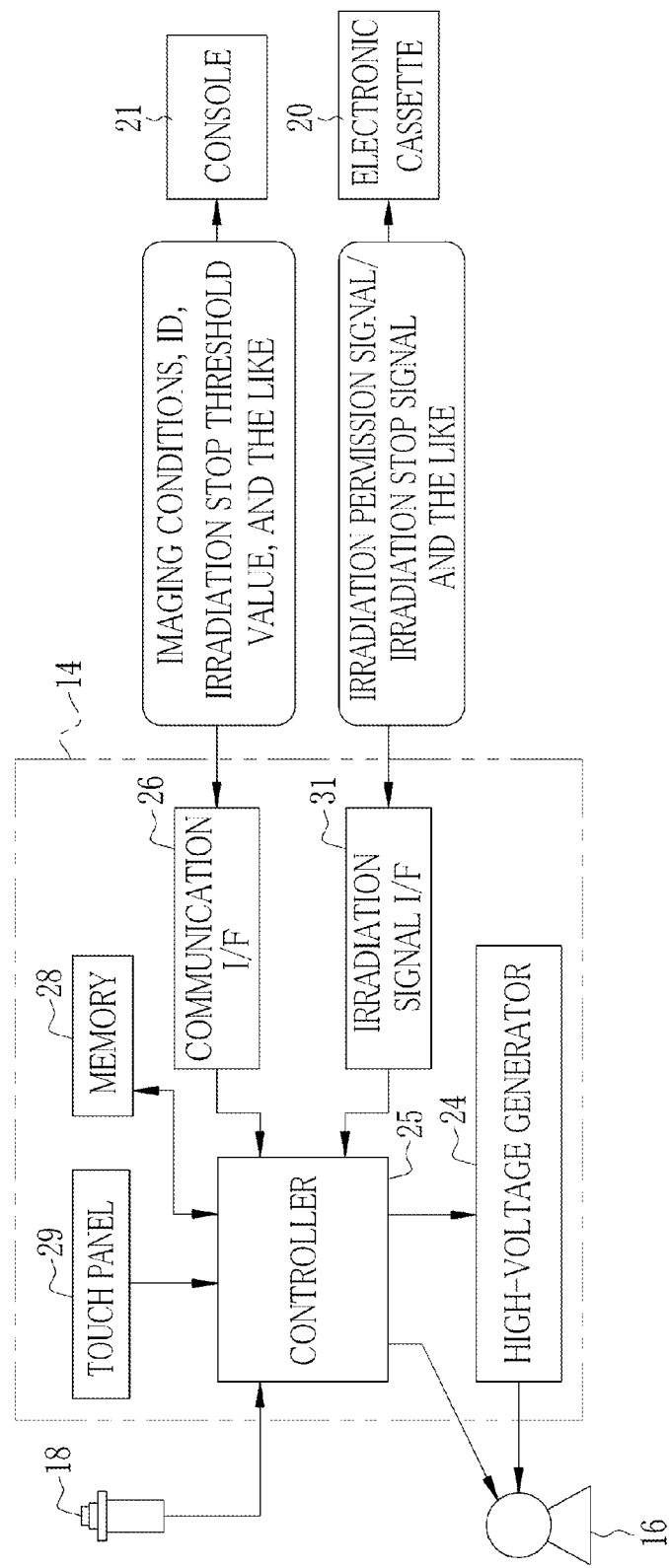
FIG. 3 is a diagram showing the internal structure of a source controller, and the relation of connection between the source controller and other devices.

As shown in FIG. 3, the source controller 14 includes a high-voltage generator 24, a controller 25, and a communication I/F 26. The high-voltage generator 24 generates a high tube voltage by multiplying an input voltage using a transformer, and supplies the X-ray source 16 with the high tube voltage through a high voltage cable. The controller 25 controls the tube voltage for determining a energy spectrum of the X-rays irradiated from the X-ray source 16, a tube current for determining an irradiation amount of the X-rays per unit of time, and an irradiation time of the X-rays. The communication I/F 26 mediates transmission and reception of fundamental information and signals to and from the console 21.

The irradiation switch 18, a memory 28, and a touch panel 29 are connected to the controller 25. The irradiation switch 18 is a switch to be operated by an operator such as a radiological technician at the time of starting the X-ray imaging. The irradiation switch 18 is, for example, a two-step push-button switch. Upon a first-step press of the irradiation switch 18, a warm-up start signal is issued to start warming-up of the X-ray source 16. Upon a second-step press, an irradiation start signal is issued to make the X-ray source 16 start X-ray irradiation. These signals are inputted to the source controller 14 through a signal cable. Upon receiving the irradiation start signal from the irradiation switch 18, the controller 25 makes the high-voltage generator 24 start supplying electric power to the X-ray source 16.

The memory 28 stores in advance a plurality of types of imaging conditions, each including the tube voltage, the tube current, the irradiation time, and a tube current-irradiation time product (mAs value). The imaging conditions are set manually by the operator through the touch panel 29. The source controller 14 starts the control of X-ray irradiation with the tube voltage, the tube current, the irradiation time, or the tube current-irradiation time product of the set imaging condition. The electronic cassette 20, which is provided with an automatic exposure control (AEC) function, detects the X-ray dose irradiated from the X-ray source 16 per unit of time. In the case where the electronic cassette 20 determines that the accumulated X-ray dose has reached a necessary and sufficient target value, the electronic cassette 20 functions to stop the X-ray irradiation even before the irradiation time or the tube current-irradiation time product preliminarily set in the source controller 14 is not achieved.

Note that, in order to prevent a shortage of the X-ray dose because of the reason that the X-ray irradiation is stopped before the accumulated X-ray dose has reached the target value and a decision to stop the X-ray irradiation is made through the AEC function, the irradiation time or the tube current-irradiation time product to be set in the source controller 14 has a value with a margin. The maximum value of the irradiation time set for the body part to be imaged in accordance with safety regulations in the source controller 14 may be set. Note that, the imaging condition transmitted from the console 21 through the communication I/F 26 may be set.

An irradiation signal I/F 31 is connected to the electronic cassette 20 in the case where the AEC function of the electronic cassette 20 is used. In this case, upon receiving the warm-up start signal from the irradiation switch 18, the controller 25 transmits an irradiation start request signal, which inquires whether or not to permit the start of X-ray irradiation, to the electronic cassette 20 through the irradiation signal I/F 31. Upon receiving the irradiation start request signal, the electronic cassette 20 performs a preparation processing. The electronic cassette 20 transmits an irradiation permission signal to the source controller 14 in the case where the electronic cassette 20 completes the preparation processing and is ready for radiography. Upon receiving the irradiation permission signal from the electronic cassette 20 through the irradiation signal I/F 31 and further receiving the irradiation start signal from the irradiation switch 18, the controller 25 makes the high-voltage generator 24 start supplying electric power to the X-ray source 16. Further, upon receiving an irradiation stop signal from the electronic cassette 20 through the irradiation signal I/F 31, the controller 25 makes the high-voltage generator 24 stop supplying electric power to the X-ray source 16, so as to stop the X-ray irradiation. Furthermore, the controller 25 has a timer used for stopping the X-ray irradiation when the set irradiation time has elapsed, in addition to the function of stopping the X-ray irradiation upon receiving the irradiation stop signal.

Figure 4:
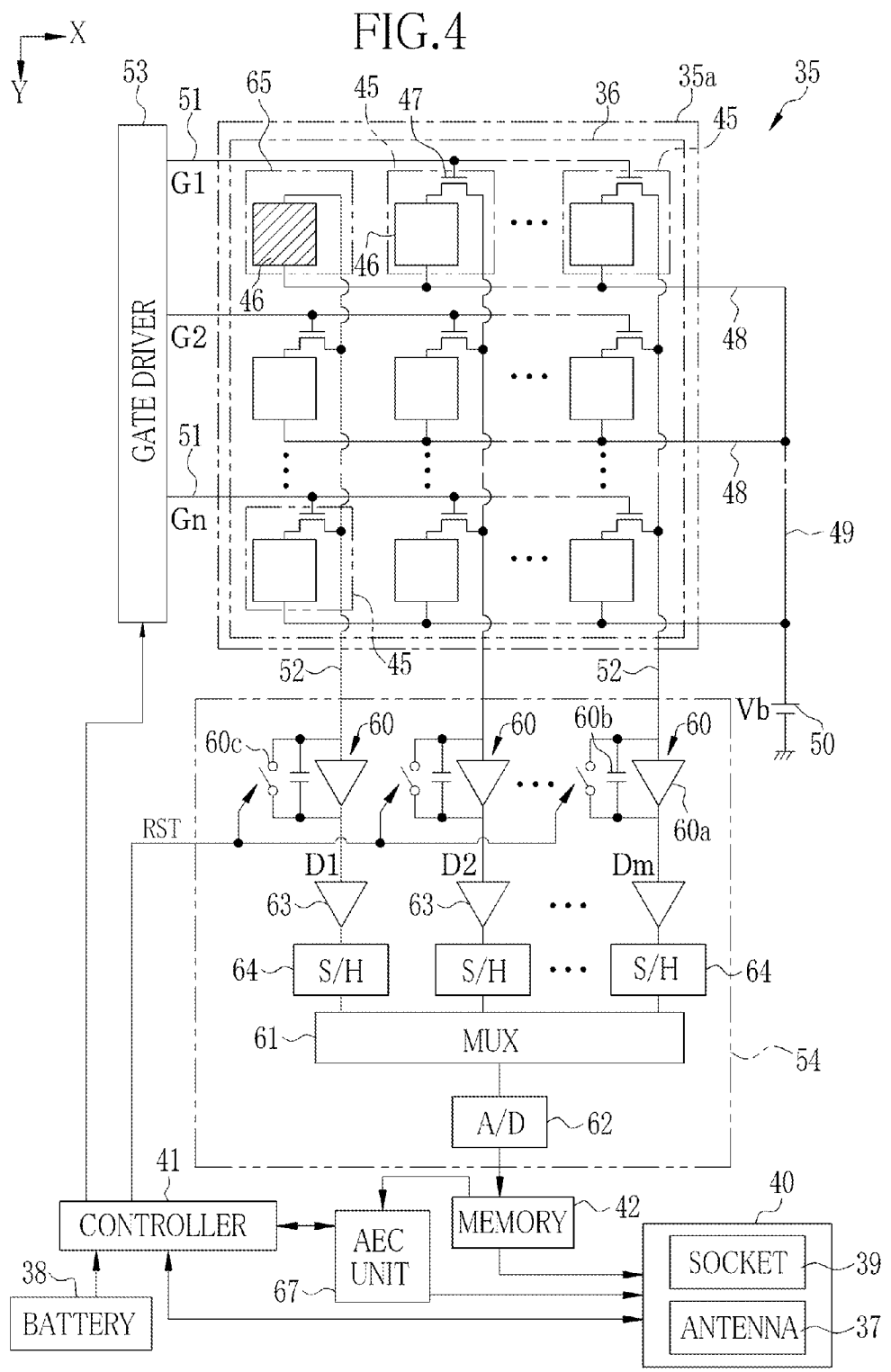
FIG. 4 is a block diagram showing the internal structure of an electronic cassette.

As shown in FIG. 4, the electronic cassette 20 contains an antenna 37 and a battery 38, and can communicate with the console 21 in a wireless manner. Radio waves for wireless communication are transmitted and received between the antenna 37 and the console 21. The battery 38 supplies electric power for operating the respective components of the electronic cassette 20. The battery 38 has a comparatively small size so as to be fitted into the thin electronic cassette 20. The battery 38 may be removed from the electronic cassette 20, and set to a dedicated cradle so as to be charged. Electric power may be supplied to the battery 38 in a wireless manner.

In addition to the antenna 37, a socket 39 is provided to the electronic cassette 20. The socket 39 is provided for wired connection to the console 21, and is used in the case where wireless communication between the electronic cassette 20 and the console 21 is disabled due to the lack of the battery level of the battery 38 or the like. In the case where a cable from the console 21 is connected to the socket 39, wired communication with the console 21 is enabled. At this time, electric power may be supplied from the console 21 to the electronic cassette 20 through the cable connected to the socket 39.

The antenna 37 and the socket 39 are contained in a communicator 40. The communicator 40 mediates transmission and reception of various kinds of information including image data and signals between the antenna 37 or the socket 39 and the controller 41 or a memory 42.

The image detector 35 is composed of a detection panel 35a and a circuit unit for controlling operation of the detection panel 35a. The detection panel 35a has a TFT (thin film transistor) active matrix substrate. On this substrate, a plurality of pixels 45 for accumulating signal charges corresponding to the received X-ray dose are arranged to constitute the imaging surface 36. The plurality of pixels 45 are arranged into a two-dimensional matrix with n rows (X direction) and m columns (Y direction) at a predetermined pitch.

The detection panel 35a further has a scintillator (not shown in the drawing) which converts X-rays into visible light, and the detection panel 35a is of an indirect-conversion type in which visible light converted by the scintillator is photoelectrically converted into the pixels 45. The scintillator is made of CsI:Tl (thallium activated cesium iodide), GOS ($Gd_2O_2S$:Tb, terbium activated gadolinium oxysulfide), or the like, and is opposed to the entire imaging surface 36 having the matrix of pixels 45. Note that, the scintillator and the TFT active matrix substrate may be disposed according to either a PSS (Penetration Side Sampling) method in which the scintillator and the substrate are disposed in this order from the X-ray incident side, or an ISS (irradiation side sampling) method in which the substrate and the scintillator are disposed in this order, oppositely to the PSS method. Another detection panel 35a of a direct-conversion type, which has a conversion layer (amorphous selenium or the like) for directly converting the X-rays into the electric charges without using the scintillator, may be used instead.

Each of the pixels 45 includes a photodiode 46 which is a photoelectric conversion element for generating the electric charges (electron-hole pairs) upon incidence of the visible light, and a thin film transistor (TFT) 47 as a switching element.

The photodiode 46 has a structure in which a semiconductor layer (for example, of a PIN (p-intrinsic-n) type) for generating electric charges, and an upper electrode and a lower electrode with the semiconductor layer interposed therebetween are disposed. In the photodiode 46, the TFT 47 is connected the lower electrode, a bias line 48 is connected to the upper electrode, and the bias lines 48 are provided for the number of rows (n rows) of the pixels 45 in the imaging surface 36, and coupled to a bus 49. The bus 49 is connected to a bias power supply 50. A bias voltage Vb is applied from the bias power supply 50 to the upper electrode of the photodiode 46 through the bus 49 and the bias line 48 as a subordinate of the bus 49. With the application of the bias voltage Vb, an electric field is generated in the semiconductor layer, and the electric charges (electron-hole pairs) generated in the semiconductor layer by photoelectric conversion are moved to the upper electrode and the lower electrode, one of which has positive polarity, and the other of which has negative polarity, and thereby the electric charges are accumulated in the photodiode 46.

The TFT 47 has a gate electrode connected to a scanning line 51, a source electrode connected to a signal line 52, and a drain electrode connected to the photodiode 46. The scanning lines 51 and the signal lines 52 are wired in a lattice shape, in which the scanning lines 51 are provided for the number of rows (n rows) of the pixels 45 in the imaging surface 36, and the signal lines 52 are provided for the number of columns (m columns) of the pixels 45 in the imaging surface 36. The scanning lines 51 are connected to a gate driver 53, and the signal lines 52 are connected to a signal processing circuit 54.

The image detector 35 is provided with the circuit unit including the controller 41, the gate driver 53, the signal processing circuit 54, and the like. The controller 41 drives the TFT 47 through the gate driver 53 to make the detection panel 53a carry out an accumulation operation for accumulating the signal charges corresponding to the received X-ray dose in the pixels 45, a readout operation (actual readout operation) for reading out the signal charges from the pixels 45, and a reset operation (idle readout operation).

In the accumulation operation, the signal charges are accumulated in the pixels 45 while the TFTs 47 are turned off. In the readout operation, the gate driver 53 sequentially issues gate pulses G1 to Gn each of which drives the TFTs 47 of the same row at a time. Thereby, the scanning lines 51 are activated, on a row-by-row basis, and the TFTs 47 connected to the activated scanning line 51 are turned on, on a row-by-row basis. The time period for which the TFTs 47 are in an on state is defined by a pulse width of the gate pulse. Upon elapse of the time period defined by the pulse width, the TFTs 47 return to be in an off state. When the TFTs 47 are turned on, the electric charges accumulated in the photodiodes 46 of the pixels 45 are read out to the signal line 52, and inputted to the signal processing circuit 54.

The signal processing circuit 54 includes integration amplifiers 60, a multiplexer (MUX) 61, an A/D converter (A/D) 62, and the like. The integration amplifier 60 is connected to each of the signal lines 52 on a one-by-one basis. Each of the integration amplifier 60 is composed of an operational amplifier 60a and a capacitor 60b connected between input and output terminals of the operational amplifier 60a. The signal line 52 is connected to one of the input terminals of the operational amplifier 60a. The other of the input terminals of the operational amplifier 60a is connected to aground (GND). A reset switch 60c is connected in parallel with the capacitor 60b. Each of the integration amplifiers 60 integrates the electric charges inputted from the signal lines 52, converts the electric charges into voltage signals D1 to Dm, and outputs the voltage signals D1 to Dm. The MUX 61 is connected to the output terminal of the operational amplifier 60a in each column through an amplifier 63 and a sample-and-hold (S/H) section 64. The A/D converter 62 is connected to the output side of the MUX 61.

The MUX 61 selects one of the integration amplifiers 60 sequentially from a plurality of the integration amplifiers 60 connected in parallel thereto, and inputs the voltage signals D1 to Dm outputted from the selected integration amplifier 60 to the A/D converter 62 in a serial manner. The A/D converter 62 converts the inputted voltage signals D1 to Dm into digital data, and outputs the digital data to the memory 42 embedded in the electronic cassette 20. An amplifier may be connected between the MUX 61 and the A/D converter 62.

After the MUX 61 reads out the voltage signals D1 to Dm in one of the rows from the integration amplifier 60, the controller 41 outputs a reset pulse RST to the integration amplifier 60 to turn on the reset switch 60c. Thus, the signal charges accumulated in the capacitor 60b in the one row is discharged to be reset. After the reset of the integration amplifier 60, the gate driver 53 outputs the gate pulse of the next row to start reading out the signal charges from the pixels 45 of the next row. By sequential repetition of this operation, the signal charges are read out from the pixels 45 of every row.

After the completion of the reading out of the signal charges from every row, the image data representing the X-ray image of one frame is recorded on the memory 42. The image data is read out from the memory 42, and outputted to the console 21 through the communicator 40. Thereby, the X-ray image of the patient is detected.

Dark charges are generated in the semiconductor layer of each of the photodiodes 46 irrespective of the presence or absence of the incidence of the X-rays. Due to the application of the bias voltage Vb, the dark charges are accumulated in the photodiodes 46 of the pixels 45. The dark charges generated in the pixels 45 become noise components for the image data, and therefore the reset operation is carried out to remove the dark charges. The reset operation is an operation to discharge the dark charges generated in the pixels 45 through the signal lines 52.

The reset operation is carried out by a sequential reset method, for example, by which the pixels 45 are reset on a row-by-row basis. In the sequential reset method, as with the readout operation of the signal charges, the gate driver 53 sequentially issues the gate pulses G1 to Gn to the scanning lines 51 to turn on the TFTs 47 of the pixels 45 on a row-by-row basis. While the TFT 47 is turned on, the dark charges flow from the pixel 45 through the signal line 52 into the capacitor 60b of the integration amplifier 60. In the reset operation, in contrast to the readout operation, the MUX 61 does not read out the electric charges accumulated in the capacitor 60b. In synchronization with the issue of each of the gate pulses G1 to Gn, the controller 41 outputs the reset pulse RST to turn on the reset switch 60c. Thereby, the electric charges accumulated in the capacitor 60b are discharged, and the integration amplifier 60 is reset.

Instead of the sequential reset method, a parallel reset method or a all-pixels reset method may be used. In the parallel reset method, a plurality of rows of pixels are grouped together, and the reset operation is sequentially carried out in each of the groups, so as to concurrently discharge the dark charges from the rows for the number of the groups. In the all-pixels reset method, the gate pulse is inputted to every row to discharge the dark charges from every pixel at a time. The parallel reset method and the all-pixels reset method allow speeding up of the reset operation.

At the timing at which the irradiation start request signal from the controller 25 of the source controller 14 is received, the controller 41 makes the detection panel 35a carry out the reset operation, and returns the irradiation permission signal to the source controller 14. At the timing at which the irradiation start signal is received, the operation of the detection panel 35a is shifted from the reset operation to the accumulation operation.

The image detector 35 includes, in addition to the normal pixels 45 connected to the signal lines 52 through the TFTs 47 as described above, a plurality of detection pixels 65 connected to the signal lines 52 in a short-circuited manner without passing through the TFTs 47 in the same imaging surface 36. The detection pixels 65 are used so as to detect the dose of the X-rays having passed through the patient M and entered the imaging surface 36, and function as dose detection sensors. The detection pixels 65 occupy several percentage of the pixels 45 in the imaging surface 36. The detection pixel 65 of this embodiment is the same in the basic structure as the pixel 45 of the photodiode 46, and therefore the detection pixel 65 and the pixel 45 can be produced through approximately the same manufacturing processing.

Figure 5:
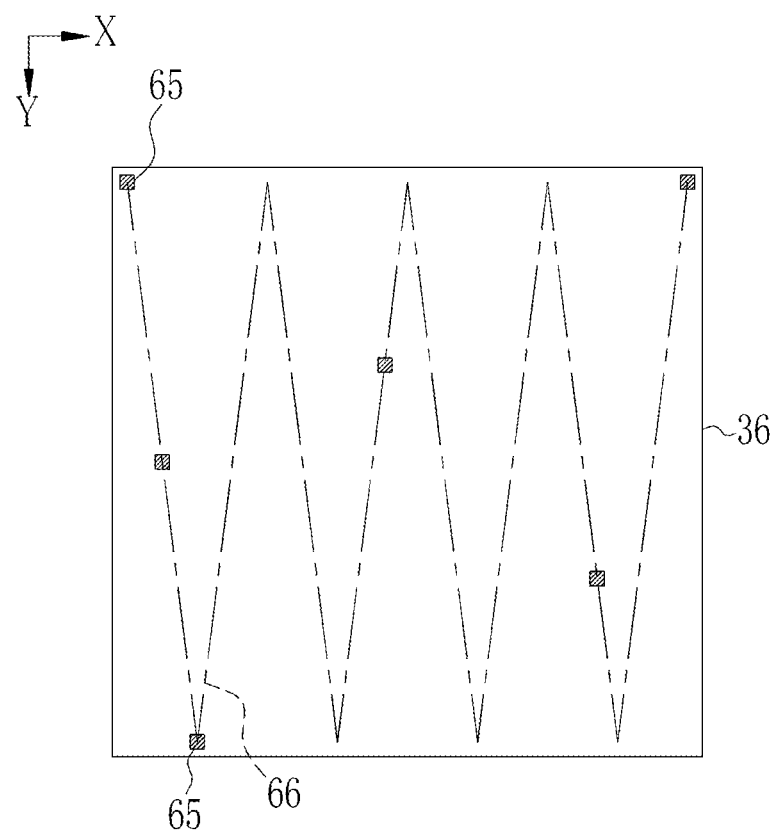
FIG. 5 is an explanatory view showing arrangement of detection pixels of an image detector.

As shown in FIG. 5, the detection pixels 65 are disposed along a waveform line 66 that is horizontally symmetric with respect to the center of the imaging surface 36 as shown by a broken line, so as to be uniformly distributed in the imaging surface 36 without being localized. One detection pixel 65 is laid out in the column of the pixels 45 connected to the single signal line 52. The column having the detection pixel 65 is arranged at intervals of two to three columns having no detection pixel 65, for example. The position of the detection pixel 65 is already known at the time of manufacturing the image detector 35, and the image detector 35 has a nonvolatile memory (not shown) that stores in advance the position (coordinates) of every detection pixel 65 in the imaging surface 36. Note that, the disposition of the detection pixels 65 of this embodiment is shown as one example. As long as the detection pixels 65 can be uniformly distributed in the imaging surface 36, the disposition of the detection pixels 65 is arbitrarily changeable.

In FIG. 4, since no TFT 47 is provided between the detection pixel 65 and the signal line 52 and the detection pixel 65 is connected directly to the signal line 52, the signal charges generated in the photodiode 46 of the detection pixel 65 flow into the signal line 52 immediately, irrespective of whether the TFT 47 is turned on or turned off. The same applies while the TFT 47 is in the off state and the normal pixel 45 in the same row is under the accumulation operation for accumulating the signal charges. For this reason, the electric charges generated in the photodiode 46 of the detection pixel 65 constantly flow into the capacitor 60b of the integration amplifier 60 on the signal line 52 to which the detection pixel 65 is connected. During the accumulation operation by the image detector 35, the electric charges accumulated in the capacitor 60b are outputted from the detection pixel 65 to the A/D converter 62 as a voltage value through the MUX 61 at a predetermined sampling period.

The A/D converter 62 outputs the voltage value as a dose detection signal of each of the detection pixels 65 to the memory 42. The dose detection signal represents the dose of X-rays irradiated per unit of time. The dose detection signal outputted at a predetermined sampling cycle is sequentially received by the memory 42. The dose detection signal of each of the detection pixels 65, which is outputted from the A/D converter 62, is recorded on the memory 42 in association with coordinate information. The controller 41 controls the operation of an automatic exposure control (AEC) unit 67. The AEC unit 67 reads out the dose detection signal of each of the detection pixels 65 from the memory 42, and performs the AEC based on the read dose detection signals.

Figure 6:
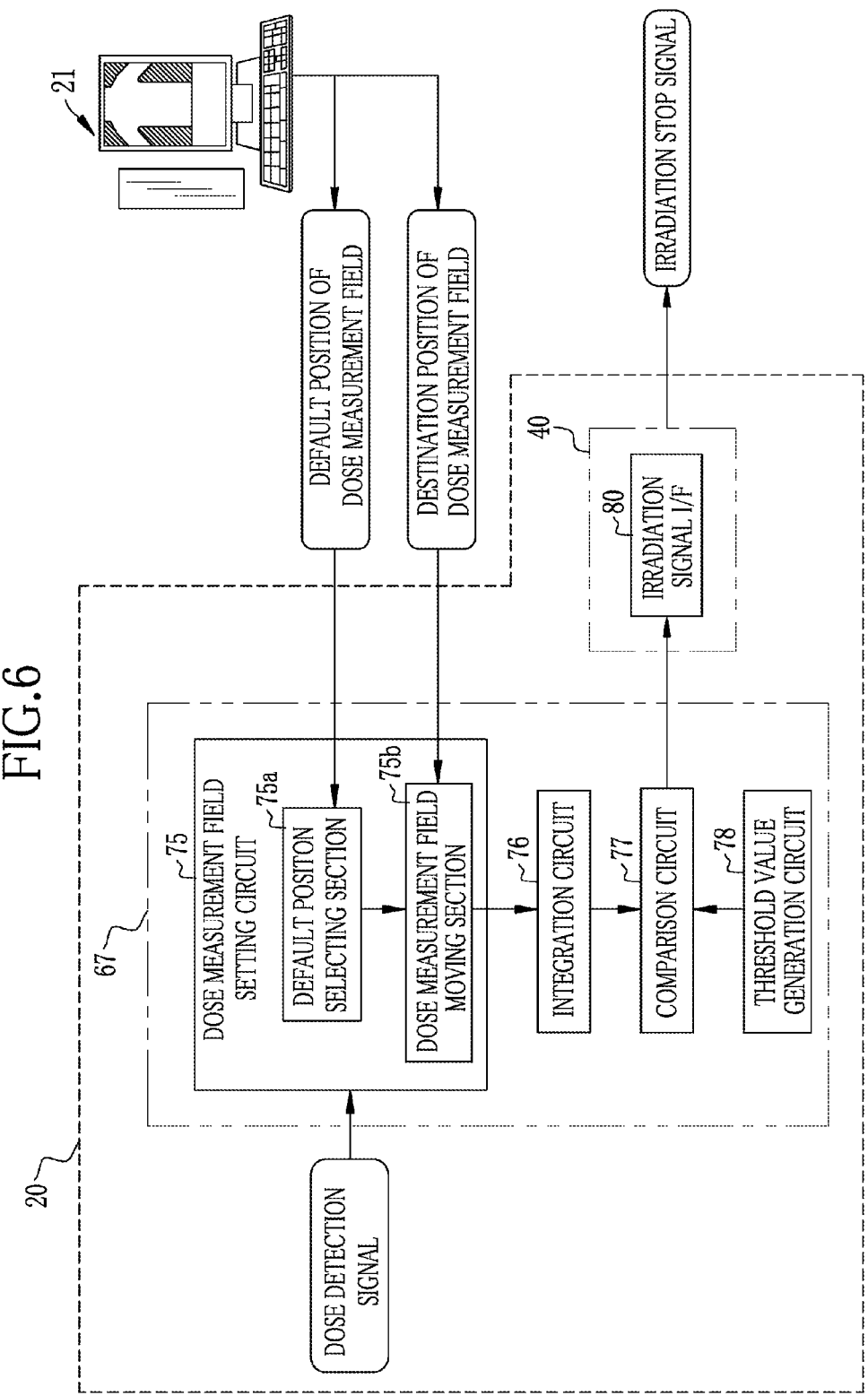
FIG. 6 is a block diagram showing an AEC unit.

In FIG. 6, the AEC unit 67 includes a dose measurement field setting circuit 75, an integration circuit 76, a comparison circuit 77, and a threshold value generation circuit 78. The dose measurement field setting circuit 75 selects one of the detection pixels 65 to be used for AEC, from among the plurality of detection pixels 65 dispersed in the imaging surface 36, based on positional information of the dose measurement field from the console 21. Thereby, the dose measurement field as a field for detecting the X-ray dose to be used for AEC in the imaging surface 36 is set. The AEC unit 67 performs AEC based on the dose detection signal of the detection pixel 65 in the set dose measurement field.

The dose measurement field setting circuit 75 includes a default position selecting section 75a for selecting a default position of the dose measurement field in the imaging surface 36 based on information relating to the default position of the dose measurement field provided from the console 21, and a dose measurement field moving section 75b for moving the position of the dose measurement field selected by the default position selecting section 75a based on information relating to a destination position provided from the console 21. Note that, the destination position is a position to which the dose measurement field is moved. The default position of the dose measurement field is set for each of the body parts to be imaged, and the default position in accordance with the body part to be imaged set in the console 21 is provided. Further, as described later, the default position of the dose measurement field is set on the assumption that the body part of the patient M to be imaged is appropriately positioned with respect to the electronic cassette 20. The dose measurement field moving section 75b moves the position of the dose measurement field to the destination position provided from the console 21.

The integration circuit 76 calculates an average value of the dose detection signals of the detection pixels 65 in the dose measurement field, and integrates the calculated average values. Calculation of the average value and integration of the average values are performed every time the dose detection signal is subjected to sampling. The comparison circuit 77 compares the integrated value of the dose detection signals from the integration circuit 76 with an irradiation stop threshold value provided from the threshold value generation circuit 78. When the integrated value has reached the threshold value, the comparison circuit 77 outputs the irradiation stop signal.

The communicator 40 has an irradiation signal I/F 80 in addition to the above-described antenna 37 and socket 39. The irradiation signal I/F 31 of the source controller 14 is connected to the irradiation signal I/F 80. The irradiation signal I/F 80 performs reception of the irradiation start request signal, transmission of the irradiation permission signal in response to the irradiation start request signal, reception of the irradiation start signal, and transmission of the irradiation stop signal from the comparison circuit 77.

Figure 7:
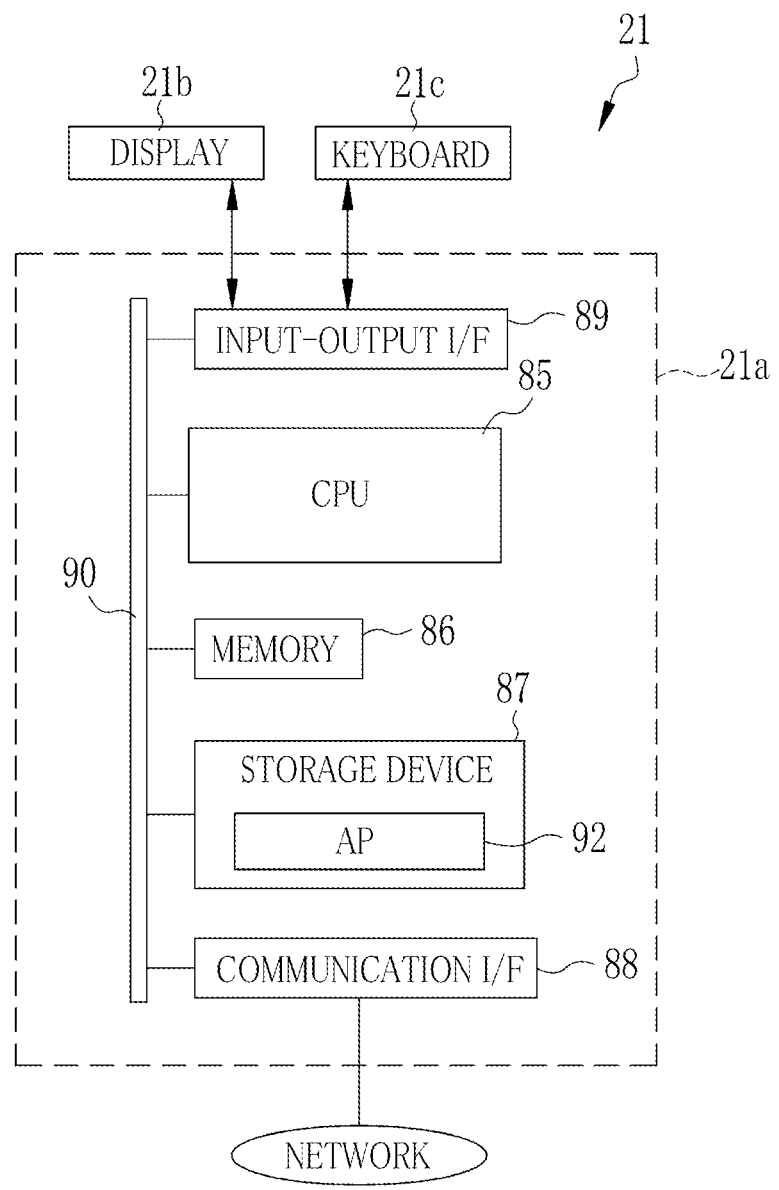
FIG. 7 is a block diagram showing the internal structure of a console.

As shown in FIG. 7, the console 21 consists of a console main body 21a, a display 21b, and a keyboard 21c. The console 21 is communicably connected to the electronic cassette 20 in a wired manner or a wireless manner, and controls the operation of the electronic cassette 20. Specifically, the console 21 transmits the information regarding the default position and the destination position of the dose measurement field to the electronic cassette 20. Further, as described later, the imaging conditions include the irradiation conditions such as the tube voltage and the tube current. In accordance with the irradiation conditions, under the control of the console 21, the electronic cassette 20 sets the conditions for the AEC and the signal processing of the image detector 35 (such as the gain of the amplifier for amplifying the voltage corresponding to the accumulated signal charges). Further, the console 21 controls the power on/off of the electronic cassette 20, mode switching to a power saving mode or an imaging preparatory state, or the like.

The console 21 performs various kinds of image processing, such as offset correction, gain compensation, and defect correction, on the X-ray image data transmitted from the electronic cassette 20. In the defect correction, the pixel value of the column in which the detection pixel 65 is provided is interpolated with the pixel value of the adjacent column in which no detection pixel 65 is provided. The X-ray image subjected to the image processing is displayed on a display 21b, and further, the data thereof is stored in a data storage such as a storage device 87 and a memory 86 in the console main body 21a, and an image storage server connected to the console 21 through a network. Note that, the image processing described above may be performed in the electronic cassette 20.

The console 21 receives the input of an examination order containing information relating to the sex, age, body part to be imaged, and imaging objective of a patient, and displays the examination order on the display 21b. The examination order is inputted from an external system, such as HIS (Hospital Information System) or RIS (radiation information system), which manages patient information or examination information relating to radiographic examination, or is inputted manually by an operator. The examination order includes a body part to be imaged such as head, chest, and abdomen, and an imaging direction such as front, side, oblique, PA (X-rays are irradiated from the rear of the object), and AP (X-rays are irradiated from the front of the object). The operator confirms the details of the examination order on the display 21b, and inputs the imaging conditions corresponding to the details through the keyboard 21c.

As shown in FIG. 8, in the console 21, the imaging conditions may be set for each of the body parts to be imaged. The imaging conditions include the tube current, the tube voltage, the dose measurement field of the detection pixel 65, the irradiation stop threshold value to be compared with the integrated value of the dose detection signals of the detection pixels 65 so as to make a decision to stop the X-ray irradiation. The information regarding the imaging conditions is stored in the storage device 87. The imaging conditions in the source controller 14 are manually set by the operator with reference to the imaging conditions in the console 21, such that the imaging conditions in the source controller 14 are similar to those in the console 21.

The information specifying the default position of the dose measurement field in the imaging surface 36 is recorded as the coordinate information which specifies the region of the dose measurement field in the imaging surface 36 by the XY coordinates, for example. The XY coordinates correspond to locations of the pixels 45, including the detection pixels 65, in the imaging surface 36 of the electronic cassette 20. The X axis of the coordinate system corresponds to the direction parallel to the scanning lines 51, the Y axis corresponds to the direction parallel to the signal lines 52, and the origin (0, 0) of the coordinate system corresponds to an upper-leftmost pixel 45 in the imaging surface 36.

Figure 9A:
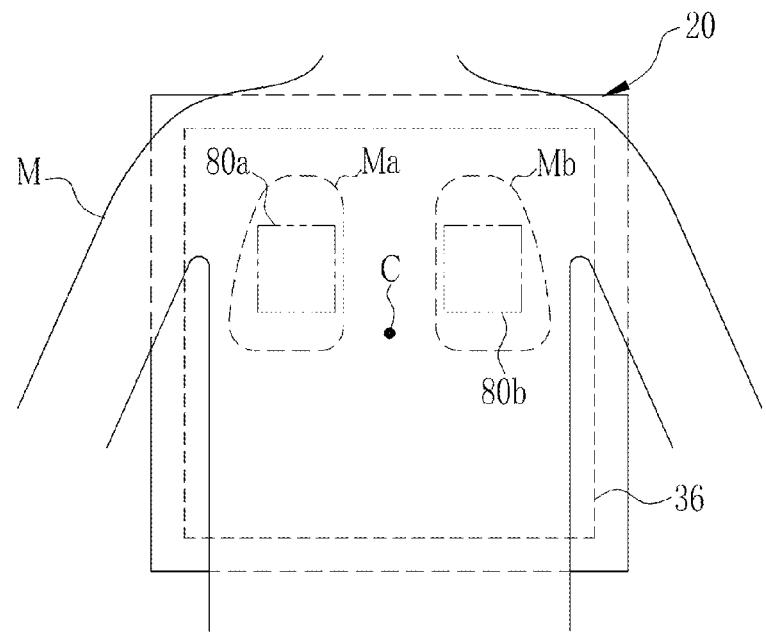
FIG. 9A is an explanatory view showing the position of a dose measurement field in a chest radiography.
Figure 9B:
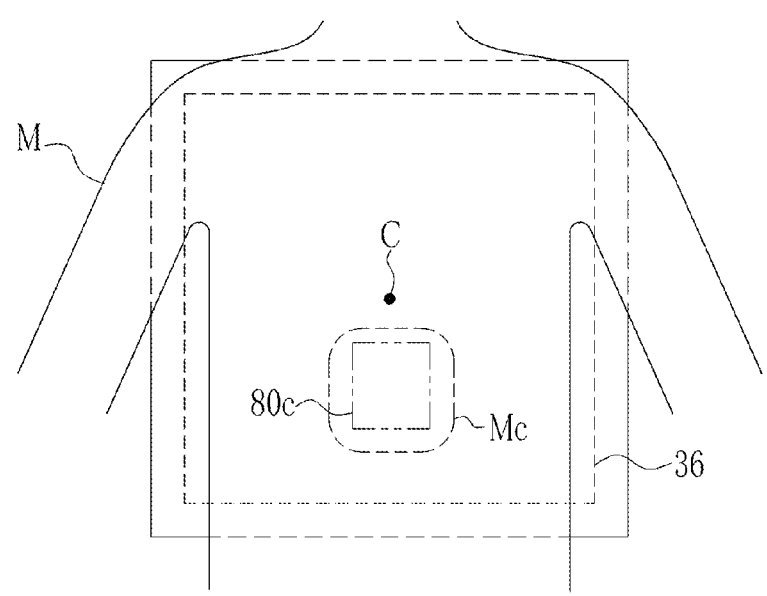
FIG. 9B is an explanatory view showing the position of a dose measurement field in an abdominal radiography.

FIG. 9A shows a state in which the body part of the patient M to be imaged is appropriately positioned with respect to the electronic cassette 20 in chest radiography, and FIG. 9B shows a state in which the body part of the patient M to be imaged is appropriately positioned with respect to the electronic cassette 20 in abdominal radiography. The dose measurement field is set to the region of interest, to which attention should be paid most at diagnosis, for each of the body parts to be imaged. For example, in the case where the body part to be imaged is a chest region, the regions corresponding to lung fields Ma and Mb of the patient M are set respectively as dose measurement fields 80a and 80b as shown by the chain double-dashed lines in FIG. 9A. Further, in the case where the body part to be imaged is an abdominal region, the region corresponding to a mediastinum Mc is set as a dose measurement field 80c as shown by the chain double-dashed line in FIG. 9B, for example.

The default position of the dose measurement field is set on the assumption that the body part of the patient M to be imaged is appropriately positioned with respect to the electronic cassette 20 as shown in FIGS. 9A and 9B. The storage device 87 which stores the imaging conditions including the default position of the dose measurement field corresponds to a default position memory section.

As shown in FIG. 7, the console main body 21a includes a CPU 85, a memory 86, the storage device 87, a communication I/F 88, and an input-output I/F 89. These components are connected to each other via a data bus 90. The display 21b and the keyboard 21c are connected to the console main body 21a through the input-output I/F 89. Note that, a mouse, a touch panel, and the like may be used together with the keyboard 21c.

The storage device 87 is a HDD (hard disk device), for example. The storage device 87 stores a control program and an application program (hereinafter called an AP) 92. The AP 92 is a program that makes the console 21 perform various functions related to the X-ray imaging, including a display processing of the examination order and the X-ray image, the image processing to be applied to the X-ray image, setting of the imaging conditions, and the like.

The memory 86 is a work memory to be used in executing processing by the CPU 85. The CPU 85 loads the control program stored in the storage device 87 into the memory 86, and executes the processing in accordance with the program, so as to make centralized control of each part of a computer. The communication I/F 88 is a network interface for performing wireless or wired transmission control with an external device such as the RIS, the HIS, the image storage server, and the electronic cassette 20.

In FIG. 10, running the AP 92 makes the CPU 85 of the console 21 function as a storage/search processing unit 95, a main control unit 96, a dose measurement field position determining unit 97, and a cassette control unit 98. The storage/search processing unit 95 executes storage processing of various kinds of data in the storage device 87 and search processing for various kinds of data stored in the storage device 87. The main control unit 96 performs overall control of the operations of the respective components of the console 21.

The dose measurement field position determining unit 97 specifies the current relative position between the X-ray source 16 and the electronic cassette 20 based on the displacement amount obtained from the displacement amount detector 19, and the position of the dose measurement field is determined in accordance with the specified current relative position. The dose measurement field position determining unit 97 includes a standard relative position setting section 97a. The standard relative position setting section 97a sets the standard relative position between the X-ray source 16 and the electronic cassette 20 in association with the default position of the dose measurement field. For example, the standard relative position is set to a position at which the main ray 17 of the X-ray source 16 is orthogonal to the imaging surface 36 of the electronic cassette 20 as well as a main ray incident position F for receiving the entrance of the main ray 17 (see FIGS. 11 and 12) is coincident with a center C of the imaging surface 36.

The purpose for moving the dose measurement field from the default position is to eliminate positional deviation generated between the default position of the dose measurement field and the region of interest in the body part to be imaged in a state that the body part of the patient M to be imaged is not appropriately positioned with respect to the electronic cassette 20. In the case where the body part of the patient M to be imaged is not appropriately positioned with respect to the electronic cassette 20, in order to make the center of the irradiation range of the X-ray source 16 (corresponding to the main ray incident position F) coincident with the center of the body part to be imaged, the X-ray source 16 is displaced so as to change the relative position between the X-ray source 16 and the electronic cassette 20.

On the ground that the relative position between the X-ray source 16 and the electronic cassette 20 is changed in the case where the body part of the patient M to be imaged is not appropriately positioned with respect to the electronic cassette 20 as described above, the dose measurement field position determining unit 97 determines the position of the dose measurement field based on the displacement amount obtained from the displacement amount detector 19.

Specifically, in the case where the positioning is performed appropriately such that the center C of the imaging surface 36 of the electronic cassette 20 is coincident with the center of the body part of the patient M to be imaged, the default position of each of the dose measurement fields 80*a* and 80*b* faces the region of interest in the body part to be imaged (the lung fields Ma and Mb in the case where the body part to be imaged is the chest portion as shown in FIG. 9A). In this state, in the case where the relative position between the X-ray source 16 and the electronic cassette 20 is set to the standard relative position, it is possible to make the center of the irradiation range of the X-ray source 16 (main ray 17) coincident with the center of the body part of the patient M to be imaged. Since the default position of the dose measurement field is in association with the standard relative position, in the case where the X-ray imaging is performed in a state that the relative position between the X-ray source 16 and the electronic cassette 20 is set to the standard relative position, the dose measurement field is not moved and remains to be at the default position.

In contrast, in the case where the center position C in the imaging surface 36 of the electronic cassette 20 is not coincident with the center of the body part of the patient M to be imaged and the relative position between the electronic cassette 20 and the body part of the patient M to be imaged is not appropriately adjusted as shown in FIG. 11A, the default positions of the dose measurement fields 80*a* and 80*b* do not correspond to the positions of the lung fields Ma and Mb as the region of interest of the patient M. In this state, in the case where the relative position between the x-ray source 16 and the electronic cassette 20 remains to be at the standard relative position in which the center C of the imaging surface 36 is coincident with the main ray incident position F, the center of the irradiation range of the X-ray source 16 (main ray 17) and the center of the body part of the patient M to be imaged are deviated from each other.

In this case, generally, the posture of the patient M is changed such that the relative position between the electronic cassette 20 and the body part of the patient M to be imaged is appropriately positioned. However, depending on the condition of the patient M, it is impossible to change the posture of the patient M, and therefore positioning cannot be performed appropriately in some cases. In order to perform X-ray imaging in this state, the X-ray source 16 is displaced such that the center of the irradiation range of the X-ray source 16 (main ray 17) is coincident with the center of the body part of the patient M to be imaged. Upon displacement of the X-ray source 16, as shown in FIG. 11B, the main ray incident position F is deviated from the center C of the imaging surface 36. However, even if the X-ray source 16 is displaced, as shown in FIG. 11A, the default positions of the dose measurement fields 80*a* and 80*b* in the imaging surface 36 do not correspond to the lung fields Ma and Mb as the region of interest in the body part to be imaged. Therefore, it becomes necessary to move the dose measurement fields 80*a* and 80*b* in the imaging surface 36 such that the dose measurement fields 80*a* and 80*b* correspond to the positions of the lung fields Ma and Mb as the region of interest, as shown in FIG. 11B.

Since the X-ray source 16 is displaced such that the main ray incident position F is located at the center of the body part of the patient M as shown in FIG. 11B, it is possible to utilize the movement distance of the main ray incident position F as the movement distance of the dose measurement fields 80*a* and 80*b*. The dose measurement field position determining unit 97 specifies the current relative position between the X-ray source 16 and the electronic cassette 20 based on the displacement amount obtained from the displacement amount detector 19, and determines the destination positions to which the dose measurement fields 80*a* and 80*b* moves from the default positions based on the movement distance of the main ray incident position F from the standard relative position shown in FIG. 11A to the current relative position shown in FIG. 11B.

There are a case where the main ray incident position F changes in accordance with the horizontal linear movement of the X-ray source 16 in parallel with the imaging surface 36 as shown in FIG. 12A, and a case where the main ray incident position F changes in accordance with the rotating movement (swinging movement) of the X-ray source 16 as shown in FIG. 12B. The height of the X-ray source 16 (at the position in the Z direction) is a distance between the X-ray source 16 and the imaging surface 36, and generally called as a SID (source image receptor distance). In the case where the X-ray source 16 rotates as shown in FIG. 12B, even if an irradiation angle α is constant, when the SID changes, the main ray incident position F also changes. The dose measurement field position determining unit 97 specifies the current relative position defined by the irradiation angle α of the X-ray source 16, the position of the X-ray source 16 in a plane in parallel with the imaging surface 36 (the position thereof in the X and Y directions), and the height of the X-ray source 16 (the position thereof in the Z direction), based on the output value representing the displacement amount outputted from the potentiometers 19*a* to 19*d* of the displacement amount detector 19, and determines the main ray incident position F at the specified current relative position.

Since the dose measurement field position determining unit 97 determines the main ray incident position F based on the output value outputted from the potentiometers 19*a* to 19*d* in consideration of the irradiation angle α and the SID, and determines the destination position of the dose measurement field based on the movement distance of the main ray incident position F as described above, it is possible to determine an appropriate destination position even when the X-ray source 16 rotates.

The standard relative position setting section 97*a* sets the standard relative position based on an operation command from the keyboard 21*c*. For example, when a setting command is inputted through the keyboard 21*c* in a state that the relative position between the X-ray source 16 and the electronic cassette 20 is set to the standard relative position, the output value outputted from the potentiometers 19*a* to 19*d* at the point of time is inputted to the standard relative position setting section 97*a*. The standard relative position setting section 97*a* stores the output value inputted from the potentiometers 19*a* to 19*d* as the standard value. Since the electronic cassette 20 is independent from the X-ray generating device 11, the SID changes in accordance with the height of the bed 33 on which the electronic cassette 20 is mounted. After the electronic cassette 20 is mounted on the bed 33, the standard relative position is set, and thereby it is possible to set the standard relative position between the X-ray source 16 and the electronic cassette 20 in view of the SID.

After the setting of standard relative position, the dose measurement field position determining unit 97 compares the output value outputted from the potentiometers 19*a* to 19*d* in accordance with the displacement amount of the X-ray source 16 with the standard value, so as to specify the current relative position. The dose measurement field position determining unit 97 calculates the movement distance of the main ray incident position F from the standard relative position (which is coincident with the center C of the imaging surface 36 in this embodiment) to the current relative position, and determines the destination positions of the dose measurement fields 80*a* and 80*b* based on the calculated movement distance. The dose measurement field position determining unit 97 outputs the destination positions of the dose measurement fields 80*a* and 80*b* as the coordinate information in the imaging surface 36. In the case where there is no change between the standard relative position and the current relative position, the dose measurement field position determining unit 97 does not output the destination position. Only in the case where there is a change between the standard relative position and the current relative position, the dose measurement field position determining unit 97 outputs the destination position. Note that, in the case where there is no change between the standard relative position and the current relative position, the destination position equivalent to the default position may be outputted.

In FIG. 10, the dose measurement field position determining unit 97 inputs the determined destination position of the dose measurement field to the cassette control unit 98. The cassette control unit 98 transmits the default position of the dose measurement field in accordance with the body part to be imaged and the destination position of the dose measurement field determined by the dose measurement field position determining unit 97 to the electronic cassette 20. Only in the case where there is a change between the standard relative position and the current relative position, the destination position of the dose measurement field is transmitted to the electronic cassette 20. Further, the cassette control unit 98 transmits the irradiation stop threshold value in accordance with the body part to be imaged to the electronic cassette 20. The storage/search processing unit 95 accesses the storage device 87 so as to retrieve and read out the specified imaging conditions, and stores the X-ray images transmitted from the electronic cassette 20. The imaging conditions include information regarding the default position of the dose measurement field in accordance with the body part to be imaged and the irradiation stop threshold value, and such information is inputted from the storage/search processing unit 95 to the cassette control unit 98.

Additionally, the console 21 has an image processing function for executing various kinds of image processing such as the offset correction, the gain compensation, and the defect correction as described above, and a communication function for mediating the communication between the source controller 14 and the electronic cassette 20. Such functions of the console 21 are achieved upon execution of a software by the CPU 85. Note that, instead of achieving the functions of each of the components by the software as in the case of this embodiment, each of the components may be a dedicated hardware. Further, at least one of the offset correction, the gain compensation, and the defect correction may be executed in the electronic cassette 20.

Next, with reference to a flowchart in FIG. 13, the procedure of X-ray imaging using the X-ray imaging system 10 is explained.

In the case where the patient M cannot move to the X-ray examination room, the X-ray generating device 11 and the electronic cassette 20 are carried to the hospital room of the patient M, so as to perform the X-ray imaging. As shown in FIG. 1, the X-ray generating device 11 is placed beside the bed 33 on which the patient M is lying. The electronic cassette 20 is inserted under the body of the patient M lying on the bed 33 (step S101). For example, in the case where the body part to be imaged is a chest region, the electronic cassette 20 is inserted under the chest region of the patient M. It is ideal that the electronic cassette 20 is positioned appropriately such that the center C of the imaging surface 36 is coincident with the center of the chest region as the body part to be imaged, as shown in FIG. 9A. However, in the case where it is impossible to perform positioning of the electronic cassette 20 appropriately, such as the case where it is impossible to change the posture of the patient M to a large extent depending on the condition of the patient M, the electronic cassette 20 is positioned in a state that the center of the chest region is deviated from the center C of the imaging surface 36, as shown in FIG. 11A.

After the X-ray generating device 11 and the electronic cassette 20 are installed, the standard relative position is set (step S102). In the setting of the standard relative position, the irradiation angle $\alpha$ of the X-ray source 16 is adjusted such that the main ray 17 of the X-ray source 16 is orthogonal to the imaging surface 36 of the electronic cassette 20, and further, the position of the X-ray source 16 in the X and Y directions is adjusted such that the main ray incident position F is coincident with the center C of the imaging surface 36 (see, FIGS. 11A and 12A). Then, the height of the X-ray source 16 (the position of the X-ray source 16 in the Z direction) is adjusted appropriately. In this state, the setting command is inputted through the keyboard 21*c* of the console 21. Upon receiving the setting command, the standard relative position setting section 97*a* sets the output value from the displacement amount detector 19 at the point of time as the standard value. Accordingly, the standard relative position is made associated with the default position of the dose measurement field.

Next, the electronic cassette 20 is powered on, and the imaging conditions are set through the keyboard 21*c* in the console 21 (step S103). In the case of chest radiography, the imaging conditions for the chest radiography are selected. Upon selection of the imaging conditions, the imaging conditions including the default position of the dose measurement field and the irradiation stop threshold value are transmitted to the electronic cassette 20 through the cassette control unit 98, and the imaging conditions are set in the electronic cassette 20. For the source controller 14, the tube voltage, the tube current, the irradiation time, a tube current-irradiation time product, and the like are set in accordance with the selected imaging conditions.

In the case where the body part to be imaged is a chest region, based on the default position of the dose measurement field inputted from the console 21, the default position selecting section 75*a* of the dose measurement field setting circuit 75 sets the dose measurement fields 80*a* and 80*b* corresponding to the lung fields Ma and Mb to the default position, as shown in FIG. 11A (step S104). As shown in FIG. 11A, in the case where the relative position between the electronic cassette 20 and the patient M is not appropriately positioned, the default positions of the dose measurement fields 80*a* and 80*b* are respectively deviated from the lung fields Ma and Mb of the patient M. Further, since the relative position between the X-ray source 16 and the electronic cassette 20 remains to be at the standard relative position, the center of the irradiation range of the X-ray source 16 (namely, the main ray 17) is also deviated from the center of the chest region of the patient M.

In view of the above, the position and the angle of the X-ray source 16 are adjusted such that the center of the irradiation range of the X-ray source 16 is coincident with the center of the chest region of the patient M. As shown in FIG. 12, upon displacement of the X-ray source 16 relative to the standard relative position, the main ray incident position F is deviated from the center C of the imaging surface 36. The displacement amount detector 19 detects the displacement amount of the X-ray source 16, and outputs the detected displacement amount to the dose measurement field position determining unit 97.

The dose measurement field position determining unit 97 specifies the current relative position between the X-ray source 16 and the electronic cassette 20 based on the detected displacement amount (step S105). The dose measurement field position determining unit 97 determines whether or not there is a change between the specified current relative position and the standard relative position (step S106). In the case where there is no change between the specified current relative position and the standard relative position (No in step S106), the dose measurement field position determining unit 97 does not determine the destination position. In this case, the dose measurement field is set to the default position. In the case where the current relative position is coincident with the standard relative position, it is considered that the positioning of the electronic cassette 20 with respect to the chest region as the body part of the patient M to be imaged is appropriately performed, and therefore the default position of the dose measurement field faces the lung fields Ma and Mb of the patient M.

In contrast, in the case where there is a change between the specified current relative position and the standard relative position (Yes in step S106), the dose measurement field position determining unit 97 determines the main ray incident position F at the specified current relative position, and calculates the movement distance of the main ray incident position F from the standard relative position. Then, based on the calculated movement distance, the dose measurement field position determining unit 97 determines the destination positions of the dose measurement fields 80a and 80b (step S107). The dose measurement field position determining unit 97 transmits the determined destination position to the electronic cassette 20 through the cassette control unit 98.

The dose measurement field moving section 75b of the dose measurement field setting circuit 75 moves the positions of the dose measurement fields 80a and 80b based on the destination positions of the dose measurement fields 80a and 80b received from the console 21, as shown in FIG. 11B (step S108). Thereby, the dose measurement fields 80a and 80b face the lung fields Ma and Mb of the patient M.

Upon completion of the preparation for radiography, the operator pushes the irradiation switch 18 by one step. Thereby, the warm-up start signal is transmitted to the source controller 14 to start warming-up of the X-ray source 16. Upon elapse of a predetermined period of time, the irradiation switch 18 is pushed by two steps, and the irradiation start signal is transmitted to the source controller 14, so as to start X-ray irradiation (step S109).

Before the start of X-ray irradiation, the reset operation is carried out in the image detector 35 of the electronic cassette 20. Upon receiving the irradiation start signal from the source controller 14, the reset operation is transited to the accumulation operation.

Concurrently with the accumulation operation by the image detector 35, the AEC unit 67 starts AEC based on the dose detection signal of the detection pixel 65 in the electronic cassette 20 (step S110). During the AEC, the dose detection signal of the detection pixel 65 is subjected to sampling at a predetermined sampling cycle, and successively outputted to the memory 42. The dose measurement field setting circuit 75 selects the dose detection signal of the detection pixel 65 present in the set dose measurement field from among the dose detection signals of the plurality of detection pixels 65 in the memory 42, and outputs the selected dose detection signal to the integration circuit 76. In the integration circuit 76, the average values of the dose detection signals are integrated (step S1101).

The threshold value generation circuit 78 outputs the irradiation stop threshold value provided by the cassette control unit 98 to the comparison circuit 77. The comparison circuit 77 compares the integrated value of the dose detection signals received from the integration circuit 76 with the irradiation stop threshold value received from the threshold value generation circuit 78 (step S1102), and outputs the irradiation stop signal at the point of time when the integrated value reaches the threshold value (Yes in step S1103) (step S1104). The irradiation stop signal is transmitted to the irradiation signal I/F 31 of the source controller 14 through the irradiation signal I/F 80.

The source controller 14 stops supplying electric power to the X-ray source 16 upon receiving the irradiation stop signal, so as to stop X-ray irradiation (step S111). After the outputting of the irradiation stop signal, the electronic cassette 20 stops the accumulation operation, such that the accumulation operation is transited to the readout operation. Then, the electronic cassette 20 reads out the X-ray image, and transmits the X-ray image to the console 21 (step S112). After the readout operation, the image detector 35 restarts the reset operation. The console 21 subjects the received X-ray image to various kinds of image processing, and displays the X-ray image on the display 21b (step S112).

According to the above embodiment, even in the case where the appropriate positioning between the electronic cassette 20 and the patient M cannot be performed and the center of the body part of the patient M to be imaged is deviated from the center C of the imaging surface 36 of the image detector 35, in conjunction with the operation for displacing the X-ray source 16 such that the main ray 17 is coincident with the center of the body part of the patient M to be imaged, the position of the dose measurement field is moved in accordance with the relative position between the X-ray source 16 and the electronic cassette 20. Consequently, even in the case where the appropriate positioning between the electronic cassette 20 and the body part of the patient M to be imaged cannot be performed, it is possible to cause the dose measurement field to face the region of interest in the body part of the patient M to be imaged. Thereby, the AEC can be performed appropriately. Since the movement of the dose measurement field is performed in conjunction with the operation for displacing the X-ray source 16, the operation is simple.

Further, since the default position of the dose measurement field is set for each of the body parts to be imaged, it is possible to appropriately make the dose measurement field coincident with the position corresponding to the region of interest in accordance with the body part to be imaged. Further, since the default position of the dose measurement field is set as one of the imaging conditions and automatically set upon selection of the imaging conditions, and thereby the operation is simple.

Although the operation for setting the standard relative position is manually performed in the above embodiment, the standard relative position may be preliminarily set. In the case where the standard relative position is preliminarily set, it is preferable that the standard relative position is set at a position on which the main ray 17 of the X-ray source 16 is orthogonal to the imaging surface 36 as well as the main ray incident position F is coincident with the center C of the imaging surface 36. The reason for this is that the default position of the dose measurement field is generally set on the basis of the center C of the imaging surface 36, on the assumption that the main ray 17, the center C of the imaging surface, and the center of the body part to be imaged are coincident with each other.

The movement distance of the main ray incident position is calculated to determine the destination position of the dose measurement field in the above embodiment. However, the destination position of the dose measurement field may be determined based on the movement distance of another reference point instead of the main ray incident position.

Further, in the case where the default position of the dose measurement field is set at a position that is offset from the center C of the imaging surface 36, the standard relative position may be set in accordance with the default position of the dose measurement field. Thus, the standard relative position may vary in accordance with the default position of the dose measurement field in some cases. Additionally, as described above, in the case of using the electronic cassette 20, since the height of the bed 33 may be changed, the SID as the distance between the X-ray source 16 and the electronic cassette 20 is not fixed. Therefore, it is preferable that the standard relative position can be set at an arbitrary position, as in the case of the above embodiment.

Figure 14:
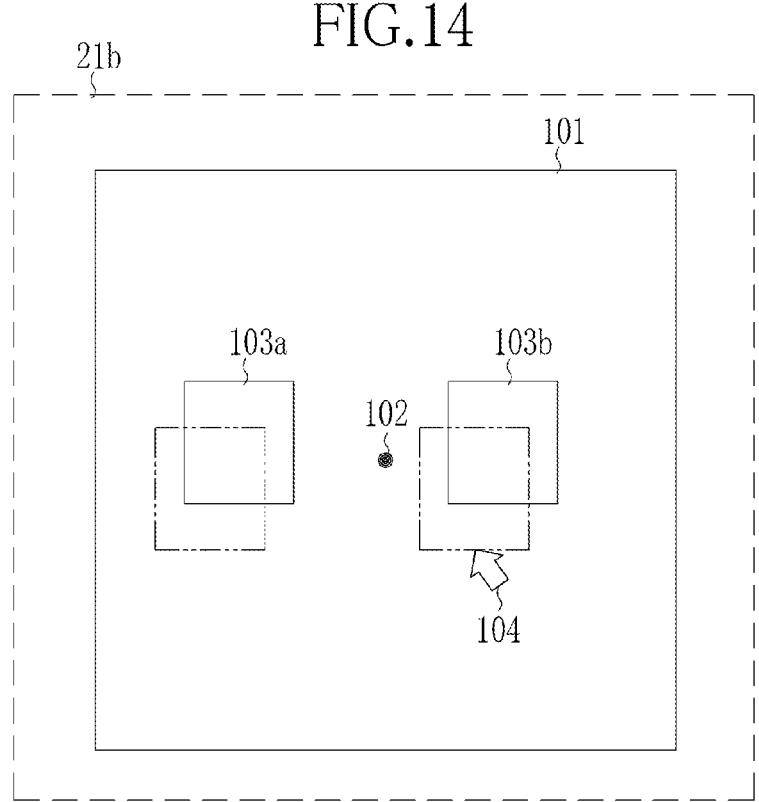
FIG. 14 is an explanatory view showing the case where the position of the dose measurement field is adjusted by a manual operation.

Further, the position of the dose measurement field may be adjusted manually independently of the displacement amount outputted from the displacement amount detector 19. In this case, for example, as shown in FIG. 14, a dose measurement field adjustment screen 101 is displayed on the display 21*b* of the console 21. A marker 102 indicating the position of the center C of the imaging surface 36, and markers 103*a* and 103*b* each indicating the position of the currently-set dose measurement field are displayed in the dose measurement field adjustment screen 101. The markers 103*a* and 103*b* can be moved by the operation through the keyboard 21*c* or a pointer 104 of a mouse. In accordance with the destination positions of the markers 103*a* and 103*b*, the destination position of the dose measurement field is transmitted from the console 21 to the electronic cassette 20.

Furthermore, the displacement of the relative position and the movement of the dose measurement field, which are constantly in conjunction with each other, may result in unavailability in some cases. As a countermeasure, switching may be performed between a state in which the displacement of the relative position and the movement of the dose measurement field are in conjunction with each other and a state in which the displacement of the relative position and the movement of the dose measurement field are not in conjunction with each other. In this case, a command for switching is given to the dose measurement field position determining unit 97 by operating the keyboard 21*c* of the console 21 or a mouse, so as to enable or disable the state in which the displacement of the relative position and the movement of the dose measurement field are in conjunction with each other.

Second Embodiment

Figure 15:
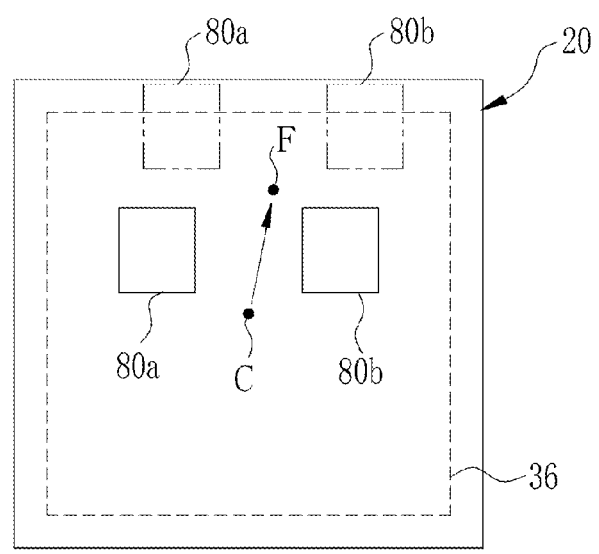
FIG. 15 is an explanatory view showing the case where a position to which the dose measurement field is moved is deviated from an imaging surface.
Figure 16:
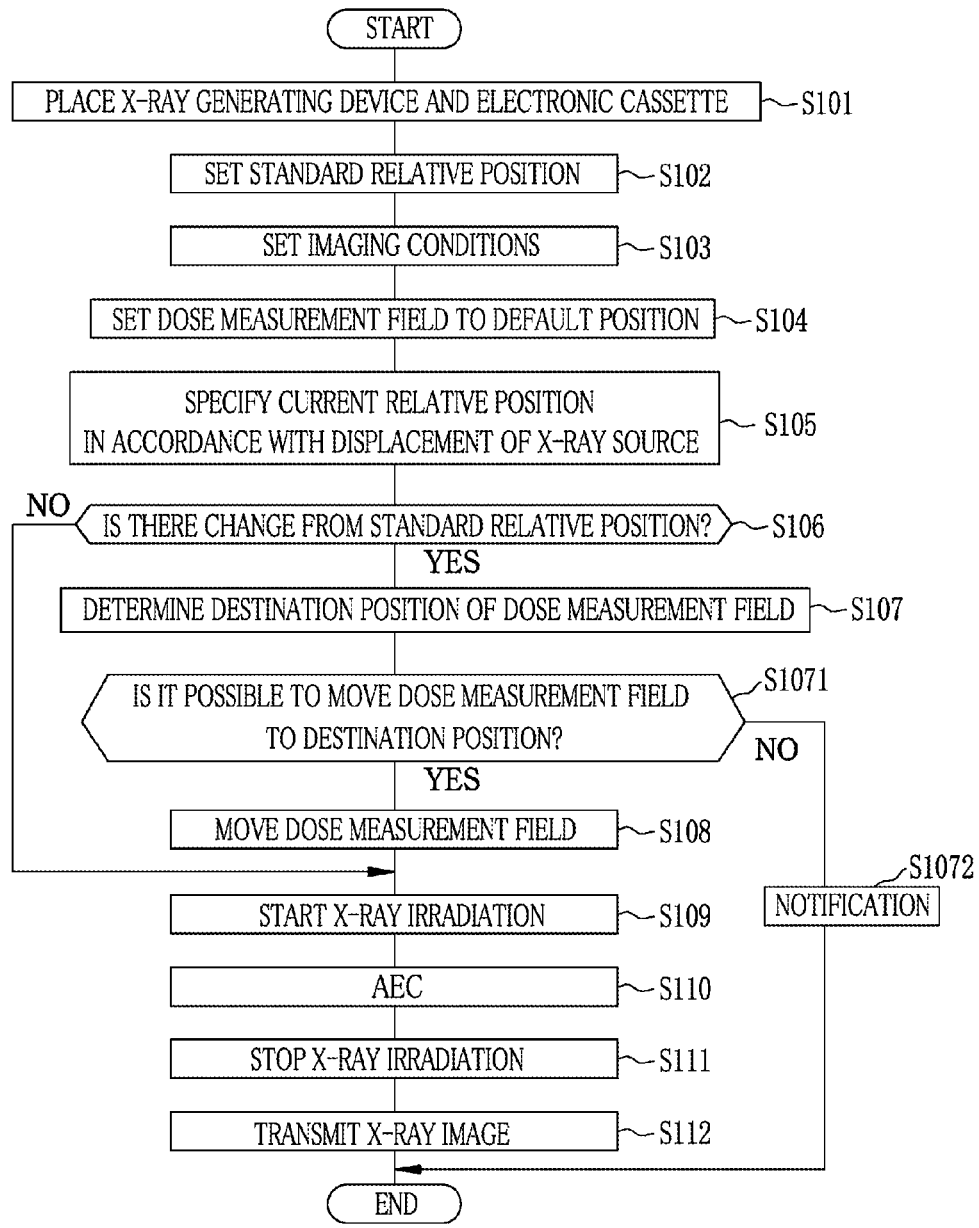
FIG. 16 is a flowchart of the processing procedure in the case shown in FIG. 15.

As shown in FIG. 15, depending on the current relative position between the X-ray source 16 and the electronic cassette 20, as the movement distance from the center C of the imaging surface 36 to the main ray incident position F is too large, the destination positions of the dose measurement fields 80*a* and 80*b* shown by the chain double-dashed lines are located outside the range of the imaging surface 36 in some cases. In this case, it is impossible to move the dose measurement fields 80*a* and 80*b*. Therefore, as shown in a flowchart in FIG. 16, after determining the destination positions of the dose measurement fields 80*a* and 80*b* in the step S107, the dose measurement field position determining unit 97 determines whether or not it is possible to move each of the dose measurement fields from the default position to the destination position in accordance with the size of the imaging surface 36 (step S1071). In the case where the dose measurement field position determining unit 97 determines that it is impossible to move each of the dose measurement fields to the destination position (No in step S1071), it is preferable to notify that effect (step S1072).

The notification is made through the display 21*b* of the console 21, for example. In this case, the display 21*b* corresponds to a notification section. The notification message indicates, for example, that the movement distance of the dose measurement field is too large and therefore it is impossible to set the dose measurement field within the imaging surface 36. The notification may be made by activating or blinking the light. Alternatively, sound may be used. In the case where such notification is made, the positioning of the electronic cassette 20 with respect to the body part to be imaged is performed again, and the position of the X-ray source 16 is adjusted again, so as to perform X-ray imaging.

Whether or not it is possible to move the dose measurement field is determined in accordance with the position and the size of the dose measurement field which are set for each body part to be imaged. Therefore, the dose measurement field position determining unit 97 makes a determination based on the default position of the dose measurement field which is set for each body part to be imaged.

Third Embodiment

Figure 17:
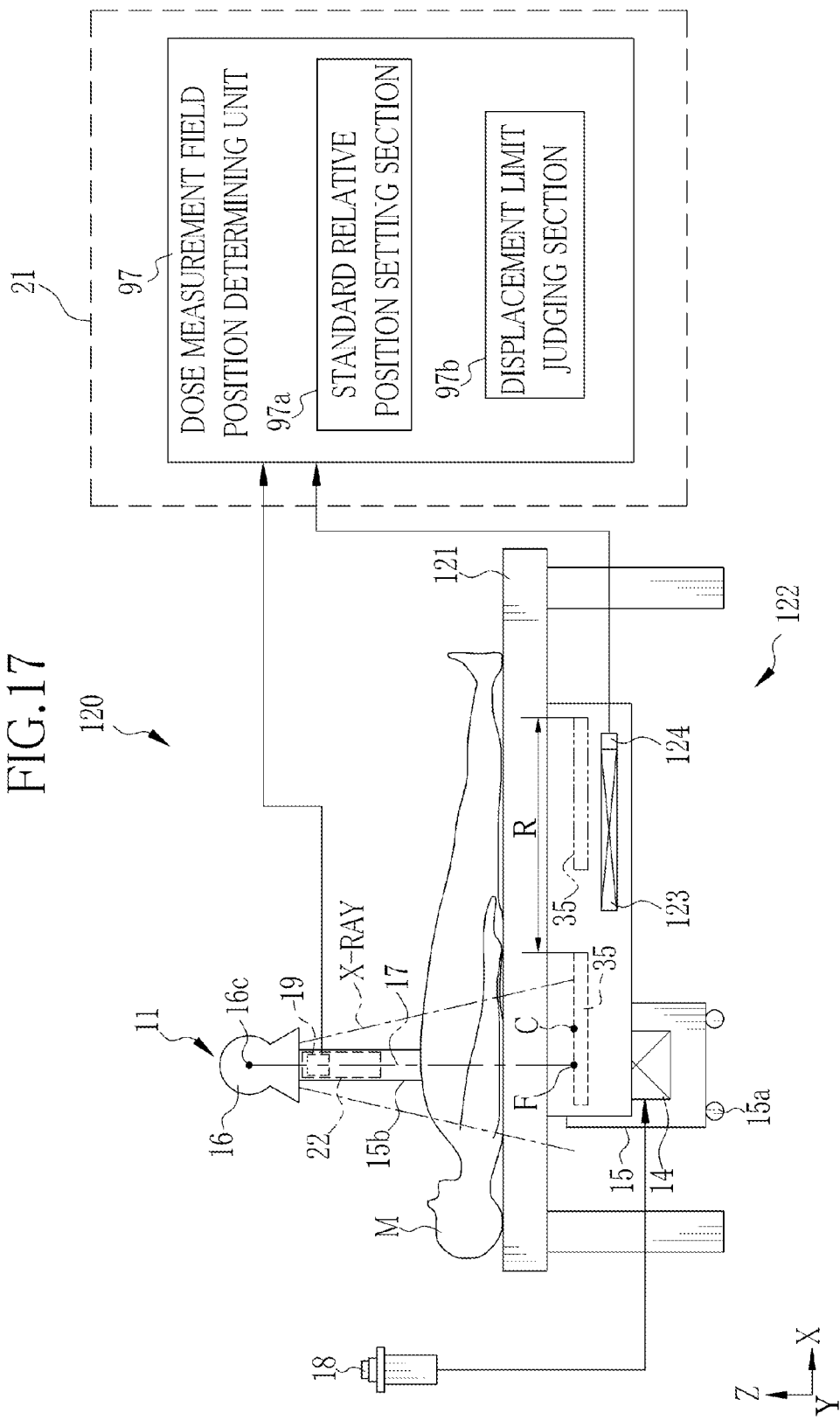
FIG. 17 is an explanatory view showing the X-ray imaging system in which both the X-ray source and the image detector are displaced.

Further, although the X-ray image detecting device is the portable electronic cassette 20 in the above embodiments, the present invention is also applicable to an X-ray imaging system 120 provided with a stationary X-ray image detecting device 122 in which the image detector 35 is incorporated into an imaging table 121 as shown in FIG. 17. The imaging table 121 is a bed-type imaging table intended for a patient in a lying posture. The imaging table 121 includes a displacement mechanism 123 for moving the image detector 35 in a horizontal direction and a displacement amount detector 124 for detecting the displacement amount of the image detector 35.

In this case, the dose measurement field position determining unit 97 acquires the displacement amount of the X-ray source 16 from the displacement amount detector 19, and the displacement amount of the image detector 35 from the displacement amount detector 124. Then, the dose measurement field position determining unit 97 sets the standard relative position in the same manner as the above embodiments, and specifies the current relative position between the X-ray source 16 and the image detector 35 based on the respective acquired displacement amounts. Here, for example, in the case where the X-ray source 16 and the image detector 35 move in the horizontal direction (i.e. the X direction) in parallel to each other by the same distance, the main ray incident position F does not move, and therefore the dose measurement field position determining unit 97 makes a determination that there is no change in the standard relative position. In the case where the main ray incident position F moves, the dose measurement field position determining unit 97 determines the destination position of the dose measurement field in accordance with the current relative position.

Further, in the case where both the X-ray source 16 and the image detector 35 are displaced as with the case of the X-ray imaging system 120, it is sometimes impossible to make the image detector 35 coincident with the center of the body part to be imaged only by moving the image detector 35 due to the restriction of installation environment of the X-ray generating device 11 and the position at which the patient M is lying on the imaging table 121. For example, as shown in FIG. 17, although it is possible to move the X-ray source 16 until the main ray 17 and the center of the body part of the patient M to be imaged are coincident with each other, it may be impossible to make the center C of the imaging surface 36 of the image detector 35 coincident with the center of the body part to be imaged by moving the image detector 35 to an edge of a movable range R. The state in which the image detector 35 is moved to the edge of the movable range R as described above is referred to as a state in which the image detector 35 has reached a displacement limit.

In the state in which the image detector 35 has not reached the displacement limitation, it is possible to make the main ray 17 of the X-ray source 16, the center C of the imaging surface 36 of the image detector 35, and the center of the body part of the patient M to be imaged coincident with each other by displacing the X-ray source 16 and the image detector 35. Therefore, it is not always necessary to move the dose measurement field.

Accordingly, it is not necessary for the dose measurement field position determining unit 97 to determine the destination position of the dose measurement field in conjunction with the displacement of the relative position while the image detector 35 does not reach the displacement limit. It is sufficient for the dose measurement field position determining unit 97 to determine the destination position of the dose measurement field in conjunction and with the displacement of the relative position, in the case where and the image detector 35 has reached the displacement limit. In this case, a displacement limit judging section 97b for judging whether or not the image detector 35 has reached the displacement limit is provided to the dose measurement field position determining unit 97. The displacement limit judging section 97b stores the information to be referred to in the judgment of the displacement limit, including the maximum and the minimum output values outputted from the displacement amount detectors 19 and 124.

Figure 18:
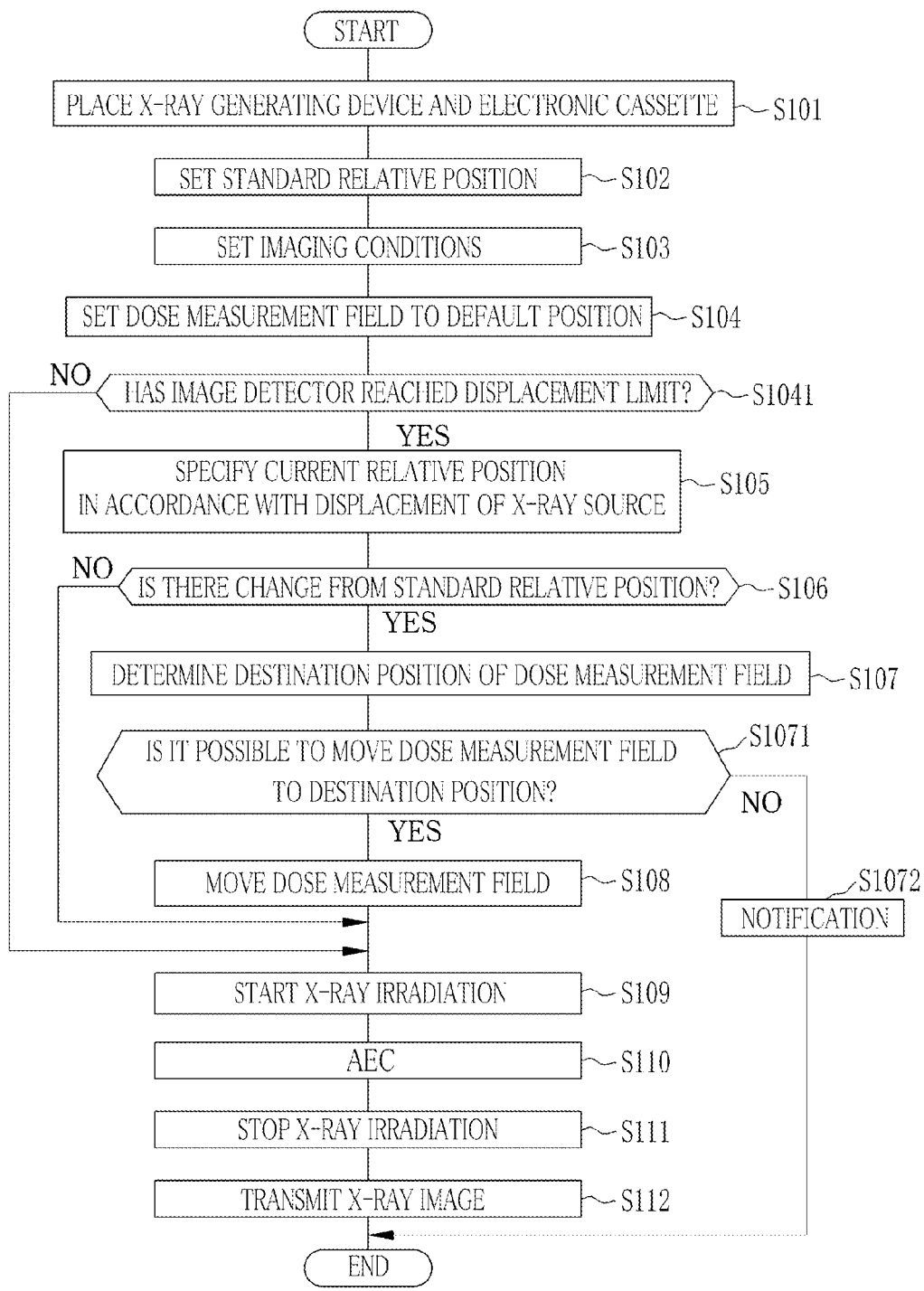
FIG. 18 is a flowchart of the processing procedure in the case where the image detector has reached a displacement limit.

As shown in FIG. 18, the dose measurement field position determining unit 97 judges whether or not the image detector 35 has reached the displacement limit based on the displacement amount acquired from each of the displacement amount detectors 19 and 124 (step S1041). In the case where the image detector 35 has not reached the displacement limit (No in step S1041), it is considered that appropriate positioning can be performed by displacing the X-ray source 16 and the image detector 35, and therefore the dose measurement field is not moved.

In contrast, in the case where the image detector 35 has reached the displacement limit (Yes in step S1041), the dose measurement field position determining unit 97 specifies the current relative position between the X-ray source 16 and the image detector 35 based on the displacement amount acquired from each of the displacement amount detectors 19 and 124 (step S105). Further, in the case where there is a change between the current relative position and the standard relative position, the dose measurement field position determining unit 97 determines the destination position of the dose measurement field (step S107). In the image detector 35, the dose measurement field is moved based on the determined destination position (step S108).

Note that, whether to move the dose measurement field is determined in view of only the displacement limit of the image detector 35, and it is not necessary to consider a displacement limit of the X-ray source 16. This is because, in the case where the X-ray source 16 has reached the displacement limit and it is impossible to make the irradiation point of the X-ray source 16 coincident with the body part to be imaged, it means a condition that the X-ray irradiation to the body part to be imaged is impossible. In this case, the body part of the patient M to be imaged is moved to the irradiation range of the X-ray source 16, and then X-ray imaging is performed.

Furthermore, although the standard relative position is set in the first and second embodiments, the setting of the standard relative position may be omitted, in the case where the X-ray imaging system is constituted by an X-ray generating device that is not movable unlike a medical equipment carrier but fixed, and a stationary X-ray image detecting device. This is because, in the case of using the fixed X-ray generating device and the stationary X-ray image detecting device, the installation positions thereof are fixed, and the standard relative positions thereof are unchanged.

Fourth Embodiment

Further, the potentiometers are used to detect the displacement amount of the relative position and specify the relative position between the X-ray source 16 and the electronic cassette 20 in the first embodiment. However, for example, as shown in FIG. 19, the X-ray source 16 may be provided with an optical camera 130 to capture an image of the electronic cassette 20 and specify the relative position between the X-ray source 16 and the electronic cassette 20 from the captured optical image.

Figure 19:
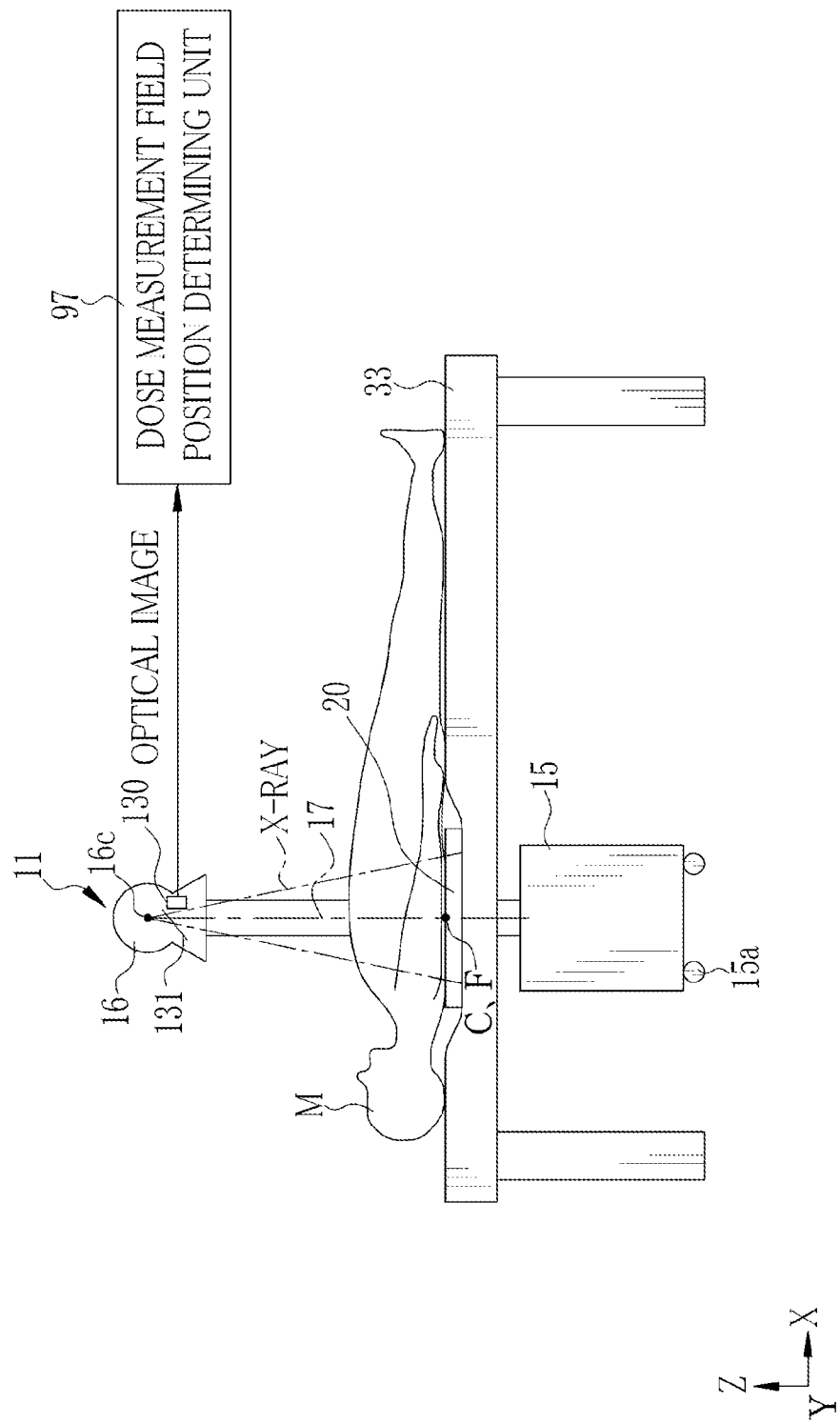
FIG. 19 is an explanatory view showing an example in which a current relative position is specified by using an optical camera.

As shown in FIG. 19, the X-ray source 16 includes the optical camera 130, and a mirror 131 that is permeable to X-rays and reflects visible rays. Firstly, the X-ray source 16 and the electronic cassette 20 are set to the standard relative position, and an image of the electronic cassette 20 is captured using the optical camera 130. The optical image captured at the standard relative position is transmitted to the dose measurement field position determining unit 97. Then, after the X-ray source 16 is displaced, an image of the electronic cassette 20 is captured again using the optical camera 130. The optical image captured after the displacement of the X-ray source 16 is also transmitted to the dose measurement field position determining unit 97. The position of the electronic cassette 20 in the optical image before the displacement of the X-ray source 16 is different from that after the displacement of the X-ray source 16. The dose measurement field position determining unit 97 subjects each of the optical images to the image processing to extract a contour of the electronic cassette 20. Further, the dose measurement field position determining unit 97 detects the displacement amount of the relative position based on the contour of the electronic cassette 20 extracted from each of the optical images before and after the displacement of the X-ray source 16, so as to specify the current relative position based on the detected displacement amount.

In this way, as the method for determining the current relative position, the optical camera 130 may be used. However, in the method with use of the optical camera 130, the image processing for extracting the contour of the electronic cassette 20 from the optical images is necessary. Since the image of the patient M is contained in the optical image, the image processing with high precision is necessary to extract the contour of the electronic cassette 20 at high accuracy, and thus there arises a concern about considerable increase in the cost. Further, in the case where the patient M covers the entire surface of the electronic cassette 20, it is impossible to extract the contour of the electronic cassette 20 from the optical image. Therefore, the potentiometer or the like is preferably used as the displacement amount detector.

Fifth Embodiment

Further, since the pixels 45 for image detection and the detection pixels 65 each functioning as the dose detection sensor exist independently of each other in the above embodiments, it is necessary to perform the defect correction. In the defect correction, the pixel value of a column in which the detection pixel 65 is provided is interpolated with the pixel value of an adjacent column in which no detection pixel 65 is provided, and thus there arises a concern about degradation in the image quality of the X-ray image. As a countermeasure, an image detector 140 configured as shown in FIG. 20 is used to eliminate the need for the defect correction.

Figure 20:
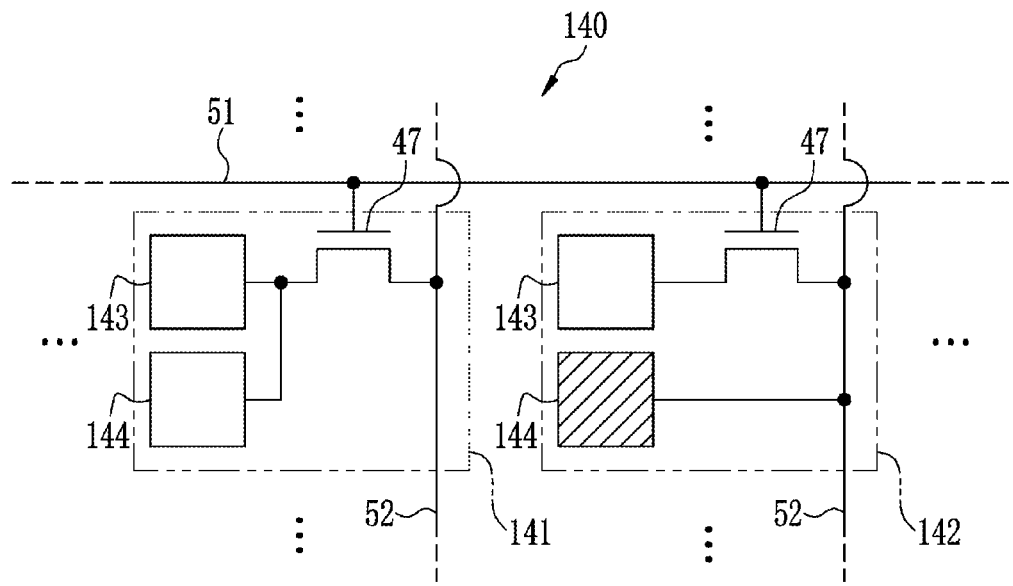
FIG. 20 is an explanatory view showing detection pixels of another embodiment.

In FIG. 20, the image detector 140 includes first pixels 141 provided for image detection and second pixels 142 functioning for both image detection and dose detection in AEC. As in the case of the pixels 45 and the detection pixels 65 in the above embodiments, the first pixels 141 and the second pixels 142 are arranged in a matrix, and the ratio between the number of the first pixels 141 and that of the second pixels 142 is appropriately determined. Each of the first pixel 141 and the second pixel 142 has photodiodes 143 and 144. The photodiodes 143 and 144 of the first pixel 141 are connected in parallel with each other, and one end of each of the photodiodes 143 and 144 is connected to the signal line 52 through the TFT 47. In contrast, although one end of the photodiode 143 of the second pixel 142 is connected to the signal line 52 through the TFT 47 in the same manner as the first pixel 141, the photodiode 144 of the second pixel 142 is directly connected to the signal line 52 without through the TFT 47. Namely, the photodiode 144 of the second pixel 142 has the same structure as that of the detection pixel 65 in the above embodiments.

The electric charges accumulated in the photodiodes 143 and 144 are read out from the first pixel 141. In contrast, only the electric charges accumulated in the photodiode 143 are read out from the second pixel 142. As the photodiode 144 of the second pixel 142 for use in the AEC does not contribute to the production of the X-ray image, the amount of electric charges accumulated in the second pixel 142 is approximately half of that in the first pixel 141 under the same incident dose in the case where an opening area of the photodiode 143 is the same as that of the photodiode 144. However, it is possible to prevent degradation in the image quality of the X-ray image as compared with the above embodiment in which the detection pixels 65 output no pixel value and the defect correction is necessary. The X-ray image can be produced without performing the defect correction by multiplying the output of the second pixel 142 by a coefficient, which is calculated in advance based on the opening area of each of the photodiodes 143 and 144 and is equivalent to the pixel value of the first pixel 141 by being multiplied by the pixel value of the second pixel 142. Thus, it is possible to almost completely eliminate adverse effect on the image quality of the X-ray image, while the adverse effect is caused by using one of the pixels, which constituting the image detector, for the AEC.

Figure 21:
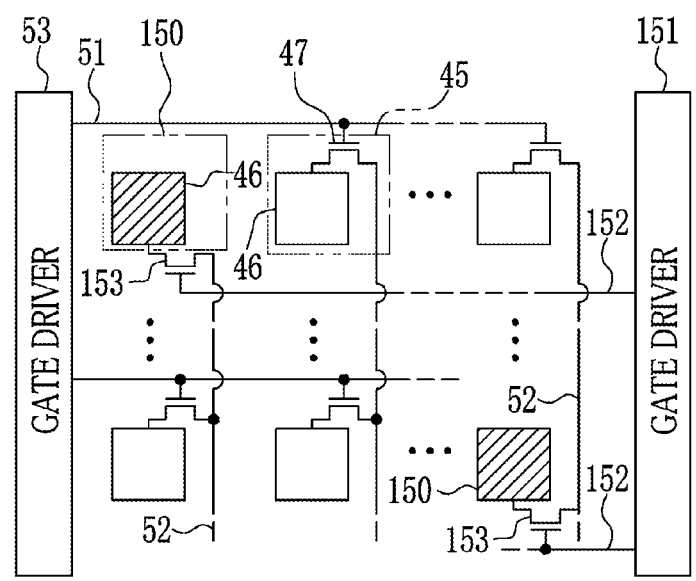
FIG. 21 is an explanatory view showing detection pixels of further another embodiment.

In the above embodiments, the detection pixel 65 that is connected to the signal line 52 directly without through the TFT 47 is used as the dose detection sensor. However, a detection pixel 150 as shown in FIG. 21 may be used, for example. The detection pixel 150 is connected to a TFT 153 driven by a gate driver 151 and a scanning line 152, which are different from those for use with the normal pixel 45, so as to read out the accumulated electric charges independently from the normal pixel 45.

Further, by using the fact that electric current flows through the bias line 48, which supplies the bias voltage Vb to each of the pixels 45, based on the amount of the electric charges generated in each of the pixels 45, the X-ray dose may be detected by monitoring the electric current flowing through the bias line 48 connected to a particular pixel 45. Alternatively, the X-ray dose may be detected based on the bias charge leaked from the pixels 45 in a state where all the TFTs 47 are turned off. In this case, an ammeter for detecting the electric current flowing through the bias line 48 is used as the dose detection sensor. Alternatively, the dose detection sensor may be disposed between adjacent pixels 45 in the imaging surface 36.

Although the console 21 and the electronic cassette 20 are separated from each other in the above embodiments, the console 21 may not be necessarily independent of the electronic cassette 20. The functions of the console 21 may be installed into the electronic cassette 20. In this case, the dose measurement field position determining unit 97 is provided to the electronic cassette 20. In the similar manner, the source controller 14 may be integrated with the console 21.

The present invention is applicable to an imaging system using another type of radiation such as γ-rays, instead of the X-rays.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. A radiation imaging system including a radiation generating device having a radiation source for irradiating radiation to an object, and a radiation image detecting device having an image detector for detecting a radiation image of the object, the image detector being formed with an imaging surface on which pixels for accumulating electric charges upon receiving the radiation are two-dimensionally arranged, the radiation imaging system comprising:

a plurality of dose detection sensors disposed on the imaging surface, for detecting a dose of the radiation to perform exposure control of the radiation image;

a dose measurement field setting section for setting a dose measurement field for the exposure control in the imaging surface by selecting at least one of the plurality of dose detection sensors;

a displacement mechanism for displacing a relative position between the radiation source and the image detector;

a displacement amount detector for detecting a displacement amount of the relative position; and a dose measurement field position determining section for specifying a current relative position as a current position of the relative position based on the displacement amount and determining a position of the dose measurement field set by the dose measurement field setting section based on the current relative position.

2. The radiation imaging system according to claim 1, further comprising:
    a default position memory section for storing a default position of the dose measurement field; and
    a standard relative position setting section for setting a standard relative position as a standard of the relative position in association with the default position of the dose measurement field, wherein
    the dose measurement field position determining section determines a destination position to which the dose measurement field moves from the default position in accordance with the specified current relative position.

3. The radiation imaging system according to claim 2, wherein the dose measurement field position determining section calculates a movement distance of a main ray incident position from the standard relative position to the current relative position, and determines the destination position of the dose measurement field based on the calculated movement distance, the main ray incident position being a position in the imaging surface of the image detector on which a main ray as a center of a radiation beam irradiated from the radiation source is incident.

4. The radiation imaging system according to claim 2, wherein the standard relative position setting section preliminarily stores the standard relative position, the standard relative position being a position at which a main ray as a center of a radiation beam irradiated from the radiation source is orthogonal to the imaging surface of the image detector as well as a main ray incident position for receiving entrance of the main ray in the imaging surface is coincident with a center of the imaging surface.

5. The radiation imaging system according to claim 2, wherein the standard relative position setting section is configured to set an arbitrary standard relative position.

6. The radiation imaging system according to claim 2, wherein the default position memory section stores the default position of the dose measurement field for each body part of the object to be imaged.

7. The radiation imaging system according to claim 2, further comprising a notification section, wherein
    the dose measurement field position determining section determines whether or not it is possible to move the dose measurement field from the default position to the destination position based on a size of the imaging surface, and
    the notification section makes a notification in the case where the dose measurement field position determining section determines it impossible to move the dose measurement field.

8. The radiation imaging system according to claim 7, wherein
    the default position memory section stores the default position of the dose measurement field for each body part of the object to be imaged, and
    the dose measurement field position determining section determines whether or not it is possible to move the dose measurement field for each body part of the object to be imaged.

9. The radiation imaging system according to claim 1, wherein the dose measurement field setting section is configured to adjust a position of the dose measurement field irrespective of the displacement amount, upon receiving a command for adjusting the position of the dose measurement field by a manual operation.

10. The radiation imaging system according to claim 2, wherein
    the displacement mechanism includes a first displacement mechanism section for displacing the radiation source,
    the displacement amount detector detects a first displacement amount as a displacement amount of the radiation source displaced by the first displacement mechanism section, and
    the dose measurement field position determining section determines the destination position of the dose measurement field based on the first displacement amount.

11. The radiation imaging system according to claim 10, wherein the first displacement amount includes at least one of a linear movement distance of the radiation source and a rotation angle of the radiation source.

12. The radiation imaging system according to claim 2, wherein
    the displacement mechanism includes a first displacement mechanism section for displacing the radiation source and a second displacement mechanism section for displacing the image detector,
    the displacement amount detector detects a first displacement amount of the radiation source displaced by the first displacement mechanism section and a second displacement amount of the image detector displaced by the second displacement mechanism section, and
    the dose measurement field position determining section determines the destination position of the dose measurement field based on the first displacement amount and the second displacement amount.

13. The radiation imaging system according to claim 12, further comprising a displacement limit judging section for judging whether or not the image detector has reached a displacement limit thereof based on the second displacement amount, wherein
    the dose measurement field position determining section does not determine the destination position of the dose measurement field in conjunction with the displacement of the relative position while the image detector does not reach the displacement limit thereof, and
    the dose measurement field position determining section determines the destination position of the dose measurement field in conjunction with the displacement of the relative position in the case where the image detector has reached the displacement limit thereof.

14. The radiation imaging system according to claim 2, wherein switching is performed between a state in which the displacement of the relative position and the movement of the dose measurement field are in conjunction with each other and a state in which the displacement of the relative position and the movement of the dose measurement field are not in conjunction with each other.

15. The radiation imaging system according to claim 1, wherein the dose detection sensor is configured to use part of the pixels in the imaging surface.

16. The radiation imaging system according to claim 1, further comprising a console for controlling the radiation image detecting device, wherein
    the dose measurement field position determining section is provided in the console, and
    the dose measurement field setting section is provided in the radiation image detecting device.

17. The radiation imaging system according to claim 16, wherein the radiation image detecting device is an electronic cassette having the image detector contained in a portable housing.

18. An operating method of a radiation imaging system including a radiation generating device having a radiation source for irradiating radiation to an object, and a radiation image detecting device having an image detector, a plurality of dose detection sensors, and a dose measurement field setting section, the image detector being formed with an imaging surface on which pixels for accumulating electric charges upon receiving the radiation are two-dimensionally arranged to detect a radiation image of the object, the plurality of dose detection sensors being disposed on the imaging surface to detect a dose of the radiation to perform exposure control of the radiation image, and the dose measurement field setting section setting a dose measurement field for the exposure control in the imaging surface by selecting at least one of the plurality of dose detection sensors, the operating method comprising:
- a displacement amount detecting step for detecting a displace amount of a relative position between the radiation source and the image detector; and
- a dose measurement field position determining step for specifying a current relative position as a current position of the relative position based on the displacement amount, and determining a position of the dose measurement field set by the dose measurement field setting section based on the current relative position.

* * * * *